United States Patent
Pellicciari et al.

(10) Patent No.: US 9,079,915 B2
(45) Date of Patent: *Jul. 14, 2015

(54) THIENYL- AND FURANYL-ISOQUINOLINONES AND METHODS FOR USING THEM

(71) Applicants: Roberto Pellicciari, Perugia (IT); Flavio Moroni, Florence (IT); Eric Christian Hansen, Ridgewood, NJ (US); Adam Matthew Gilbert, Guilford, CT (US); Peter John Larkin, Trumbull, CT (US)

(72) Inventors: Roberto Pellicciari, Perugia (IT); Flavio Moroni, Florence (IT); Eric Christian Hansen, Ridgewood, NJ (US); Adam Matthew Gilbert, Guilford, CT (US); Peter John Larkin, Trumbull, CT (US)

(73) Assignees: Robert Pellicciari, Perugia (IT); Flavio Moroni, Florence (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/106,228

(22) Filed: Dec. 13, 2013

(65) Prior Publication Data

US 2014/0107117 A1  Apr. 17, 2014

Related U.S. Application Data

(63) Continuation of application No. 12/487,309, filed on Jun. 18, 2009, now Pat. No. 8,633,215.

(60) Provisional application No. 61/073,866, filed on Jun. 19, 2008.

(51) Int. Cl.
| | |
|---|---|
| *A61K 31/4355* | (2006.01) |
| *A61K 31/4365* | (2006.01) |
| *C07D 495/04* | (2006.01) |
| *C07D 491/048* | (2006.01) |

(52) U.S. Cl.
CPC .......... *C07D 495/04* (2013.01); *C07D 491/048* (2013.01)

(58) Field of Classification Search
USPC ............................................. 514/292; 546/81
See application file for complete search history.

(56) References Cited

U.S. PATENT DOCUMENTS

| | | |
|---|---|---|
| 4,232,017 A | 11/1980 | Winters et al. |
| 6,989,388 B2 | 1/2006 | Pellicciari et al. |
| 7,501,412 B2 | 3/2009 | Fujio et al. |
| 2005/0171101 A1 | 8/2005 | Yamamoto et al. |
| 2009/0318442 A1 | 12/2009 | Pellicciara et al. |

FOREIGN PATENT DOCUMENTS

| | | |
|---|---|---|
| WO | WO-0236599 A1 | 5/2002 |
| WO | WO/2004048339 | 6/2004 |
| WO | WO-2007149907 A2 | 12/2007 |

OTHER PUBLICATIONS

Graziani et al. "Clinical Perspectives of PARP Inhibitors." *Pharma. Res.* 52(2005):109-118.
Pellicciari et al. "Towards New Neuroprotective Agents: Design and Synthesis of 4H-thieno[2,3-c] Isoquinolin-5-one Derivatives as Potent PARP-1 Inhibitors." *Il Farmaco.* 58(2003):851-858.
Summerfield et al. "Central Nervous System Drug Disposition: The Relationship Between in Situ Brain Permeability and Brain Free Fraction." *J. Pharmacol. Exp. Therapeut.* 322(2007):205-213.
Tietze et al. "Synthesis of Noval Chiral Thiophene-, Benzothiopene- and Benzofuran-Oxazoline Ligands and their Use in the Enantioselective Pd-Catalyzed Allylation." *Synlett.* 12(2002):2083-2085.
Wermuth. "Molecular Variations Based on Isoteric Replacements." *Pract. Med. Chem.* (2003):189-214.
Yamaguchi et al. "4-Phenylthiazole Derivatives Inhibit IL-6 Secretion in Osteoblastic Cells and suppress Bone Weight Loss in Ovariectomized Mice." *Bioorg. Med. Chem. Lett.* 9(1999):957-960.
Chiarugi et al. "Novel Isoquinolinone-Derived Inhibitors of Poly(ADP-Ribose) Polymerase-1: Pharmacological Characterization and Neuroprotective Effects in an In Vitro Model of Cerebral Ischemia." *J. Pharmacol. Exp. Ther.* 305,3 (2003):943-949.
Dorward, F.A. "Side Reactions in Organic Synthesis." Wiley: VCH, Weinheim (2005): p. IX of Preface.

*Primary Examiner* — Rita Desai
(74) *Attorney, Agent, or Firm* — Cooley LLP; Ivor R. Elrifi; Heidi A. Erlacher

(57) ABSTRACT

The present invention relates to substituted thienyl- and furanyl-isoquinolinones that act, for example, as modulators of poly(ADP-ribose) polymerase (PARP). The present invention also relates to processes for the preparation of substituted thienyl and furanyl-isoquinolinones and to their use in treating various diseases and disorders.

37 Claims, 4 Drawing Sheets

THIENYL- AND FURANYL-ISOQUINOLINONES AND METHODS FOR USING THEM

This application is a continuation of U.S. application Ser. No. 12/487,309, filed Jun. 18, 2009, and claims benefit of priority under 35 U.S.C. §119 (e) to U.S. Provisional Application No. 61/073,866 filed Jun. 19, 2008, each of which is hereby incorporated by reference in its entirety.

FIELD

The present invention relates to substituted thienyl- and furanyl-isoquinolinones that act, for example, as modulators of poly(ADP-ribose) polymerase (PARP). The present invention also relates to processes for the preparation of substituted thienyl- and furanyl-isoquinolinones and to their use in treating various diseases and disorders.

BACKGROUND

The poly (ADP-ribose) polymerase (PARP) family of enzymes catalyzes the post-translational modification of several nuclear proteins in response to DNA damage. PARP activation is involved in the ability of cells to repair injured DNA, yet also plays a role in the pathogenesis of various cardiovascular and inflammatory diseases. The family of PARP enzymes contains at least 5 members, termed PARP-1, PARP-2, PARP-3, tankyrase, and VPARP.

Because of PARP's role in DNA repair, and the pathogenesis of various cardiovascular and inflammatory diseases, a number of PARP inhibitors are being currently developed clinically or are already in clinical trials for the treatment of various diseases and conditions, including chronic and acute neurological and cardiovascular conditions and cancers. (Pharmacological Research Vol: 52 Issue: 1, July, 2005 pp: 109-118). A need exists for potent compounds that can inhibit PARP activity. The present invention addresses this and other needs.

SUMMARY

The present invention is directed to certain substituted thienyl and furanyl-isoquinolinones and to their use, for example, in medical treatment. In one aspect, the invention relates to substituted thienyl- and furanyl-isoquinolinones that act as modulators of PARP. The compounds can be used as PARP inhibitors to, for example, inhibit neuronal cell death in a subject. The compounds can be used, for example, to treat disease and disorders including damage due to ischemia and reperfusion, degenerative diseases, inflammation, including multiple inflammatory disease, tumor diseases, including cancer, and cardiovascular dysfunction, including myocardial infarction and atherosclerosis.

In certain aspects, the present invention is directed to compounds of Formula I:

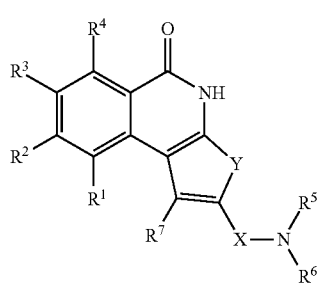

Formula I wherein:
X is $C_1$-$C_9$ alkylene, $C_2$-$C_9$ alkenylene, or $C_2$-$C_9$ alkynylene;
Y is S or O;
$R^1$ is halogen, hydroxy, $NH_2$, $C_1$-$C_6$ alkoxy, CN, or $C_1$-$C_6$ perfluoroalkyl;
$R^2$, $R^3$, and $R^4$ are independently selected from hydrogen, $C_1$-$C_6$ alkyl, halogen, hydroxy, $NH_2$, CN, $C_1$-$C_6$ perfluoroalkyl, $CO_2H$, $OR^8$, $COOR^8$, or $NHR^8$;
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl, wherein the alkyl, alkenyl and rings of the cycloalkyl, phenyl and benzyl groups are optionally substituted with one or more groups selected from hydroxy, $C_1$-$C_4$ alkoxy, —$CO_2H$, $C_1$-$C_6$ alkoxycarbonyl, $NH_2$, $C_1$-$C_6$ mono- or dialkylamino, or halogen; or
$R^5$ and $R^6$ together with the nitrogen to which they are attached form a saturated, partially unsaturated, or unsaturated 3 to 12 membered monocytic or bicyclic heterocyclic ring optionally comprising from one to three additional ring heteroatoms selected from N, O, or S, the remainder of the ring atoms being carbon atoms;
$R^7$ is hydrogen, halogen, hydroxy, $NH_2$, $C_1$-$C_3$ alkyl, $C_1$-$C_3$ alkoxy or $NO_2$;
$R^8$ is $C_1$-$C_6$ alkyl, $C_2$-$C_6$ alkenyl, or $C_3$-$C_7$ cycloalkyl wherein the alkyl, alkenyl, and rings of the cycloalkyl are optionally substituted with one or more groups selected from hydroxy, $C_1$-$C_4$ alkoxy, —$CO_2H$, $C_1$-$C_6$ alkoxycarbonyl, $NH_2$, $C_1$-$C_6$ mono- or dialkylamino, or halogen;
or a pharmaceutically acceptable salt or zwitterionic form thereof.

In other embodiments, the invention relates to compositions comprising at least one compound of the present invention and at least one pharmaceutically acceptable carrier.

In yet other embodiments, the invention is directed to methods for treating a patient having tissue damage due to ischemia and/or reperfusion; methods for treating diseases associated with tissue damage due to ischemia and/or reperfusion, including, for example, stroke, cerebral or spinal trauma (e.g., spinal cord injury), epileptic events, cerebral damage due to cardiac arrest and/or conditions arising from situations of prolonged hypotension, respiratory arrest, carbon monoxide or cyanide poisoning, drowning, or hydrocephalus; methods for treating degenerative diseases of the central nervous system, including, for example, Parkinson's disease, Alzheimer's dementia, Huntington's chorea, amyotrophic lateral sclerosis, macular degeneration and retinal ischemia; methods for treating degenerative diseases of the muscles, including, for example, muscular dystrophy; methods for treating degenerative diseases of the bones, including, for example, osteoporosis; methods for treating degenerative diseases of the vascular system, including, for example, atherosclerosis, diabetes, and diseases of the immune system present during senescence; methods for treating inflammatory diseases, including, for example, multiple sclerosis and other demyelinizing diseases, Guillain-Barre syndrome, neuralgias of the trigeminus and/or other cranial nerves, peripheral neuropathies and other chronic pain, osteoarthritis, inflammatory diseases of the intestine including, for example, Crohn's disease, ulcerative colitis, and other forms of colitis; methods for the treatment of various forms of cancer including, for example, leukemia, sarcoma primary or associated with AIDS, breast cancer, refractory solid tumors, lymphoid malignancies, brain tumors, and p53 deficient tumors.

DETAILED DESCRIPTION

Figure 1:
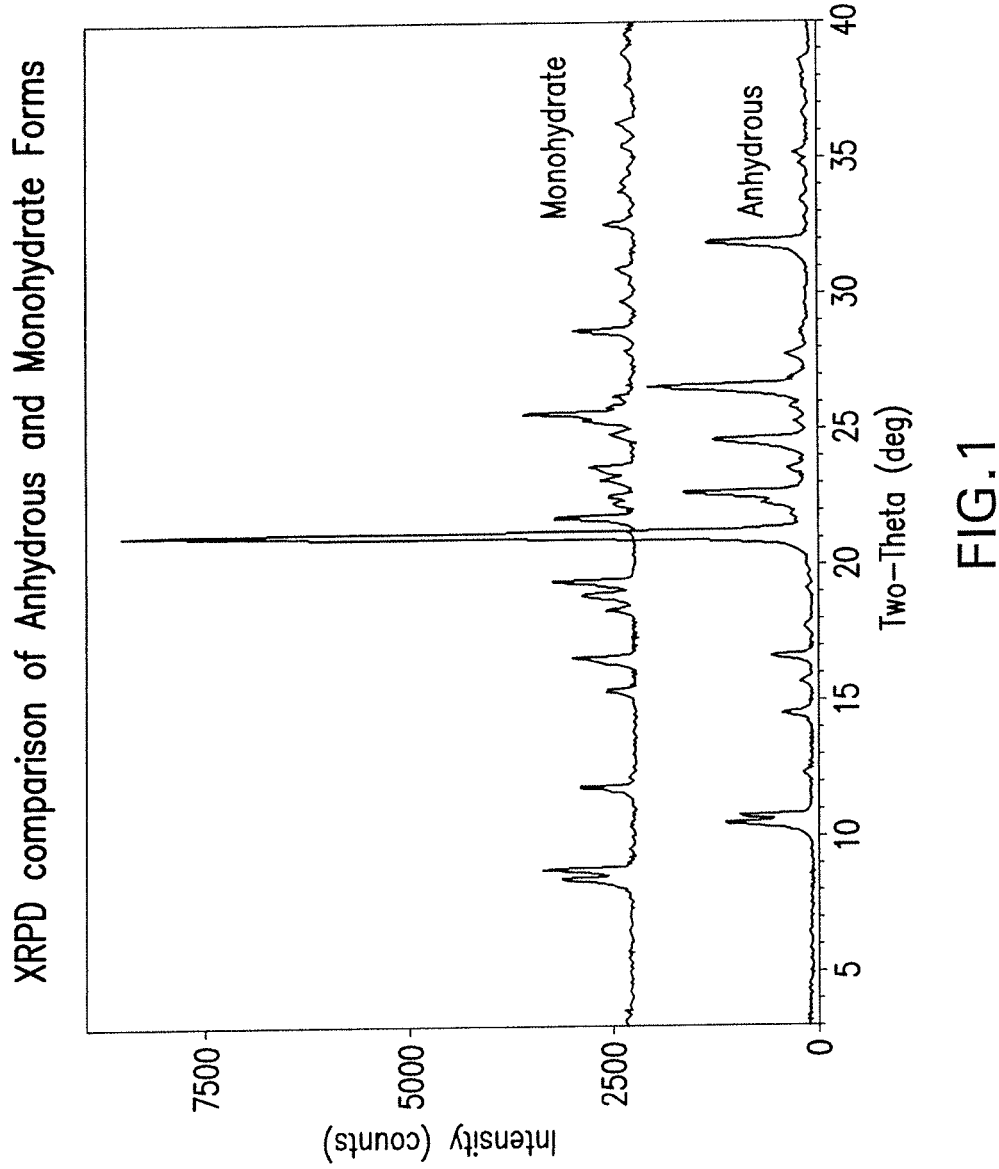
FIG. 1 shows PXRD patterns for monohydrate and anhydrous forms of 2-dimethylaminomethyl-9-hydroxythieno[2,3-c]isoquinolin-5(4H)-one.

The present invention is directed to, inter alia, substituted thienyl- and furanyl-isoquinolinones and to their use as modulators of PARP. The compounds can be used to inhibit PARP. The compounds can also be used in medical treatment to treat various disease and disorders, including those associated with neuronal cell death.

The following definitions are provided for the full understanding of terms used herein.

The term "alkyl," as used herein, refers to an aliphatic hydrocarbon chain having 1 to 12 carbon atoms, preferably 1 to 8 carbon atoms, more preferably 1 to 6 carbon atoms, and more preferably 1 to 4 carbon atoms. The term "alkyl" includes straight and branched chains. Straight chain alkyl groups have 1 to 8 carbon atoms and branched chain alkyl groups have 3 to 12 carbon atoms. Examples of alkyl groups include methyl, ethyl, n-propyl, isopropyl, n-butyl, isobutyl, sec-butyl, t-butyl, n-pentyl, isopentyl, neo-pentyl, n-hexyl, and isohexyl groups.

As used herein, the term "alkylene" refers to a bivalent alkyl radical having the general formula —$(CH_2)_n$—, where n is 1 to 10, and all combinations and subcombinations of ranges therein. The alkylene group may be straight, branched or cyclic. Non-limiting examples include methylene, methylene (—$CH_2$—), ethylene (—$CH_2CH_2$—), propylene (—$(CH_2)_3$—), trimethylene, pentamethylene, and hexamethylene. Preferred alkylene groups have from 1 to about 3 carbons.

The term "perfluoroalkyl," as used herein, refers to a straight or branched aliphatic hydrocarbon chain of 1 to 8 carbon atoms and preferably 1 to 3 carbon atoms, in which all hydrogens are replaced with fluorine, e.g. $CF_3$.

The term "alkenyl," as used herein, refers to an aliphatic straight or branched hydrocarbon chain having 2 to 12 carbon atoms that contains 1 to 3 double bonds. Examples of alkenyl groups include, but are not limited to, vinyl, prop-1-enyl, allyl, but-1-enyl, but-2-enyl, but-3-enyl, 3,3-dimethylbut-1-enyl, or 2-methylvinyl.

As used herein, the term "alkenylene" refers to an alkylene group containing at least one carbon-carbon double bond. Exemplary alkenylene groups include, for example, ethenylene (—CH=CH—) and propenylene (—CH=CHCH$_2$—). Preferred alkenylene groups have from 2 to about 3 carbons.

The term "alkynyl," as used herein, refers to an aliphatic straight or branched hydrocarbon chain having 2 to 9 carbon atoms that contains 1 to 3 triple bonds.

As used herein, the term "alkynylene" refers to an alkylene group containing at least one carbon-carbon triple bond. Exemplary alkynylene groups include, for example, acetylene (—C≡C—), propargyl (—CH2C≡C—), and 4-pentynyl (—CH2CH2CH2C≡CH—). Preferred alkynylene groups have from 2 to about 3 carbons.

The term "heterocyclic ring," as used herein, refers to a 3 to 12 membered, and more preferably 5 to 7 membered, saturated, partially unsaturated, or unsaturated monocyclic or bicyclic ring system which contains carbon ring atoms and from 1 to 4 ring heteroatoms independently selected from nitrogen, oxygen, or sulfur. The nitrogen and sulfur heteroatoms may optionally be oxidized. Heterocyclic rings include, for example, 3 to 12 membered saturated monocytic rings such as piperidine, morpholine, pyrrolidine, homopiperidine, aziridine, and azetidine.

The term "cyano," as used herein, refers to the group —CN.

The term "amino," as used herein, refers to the group —$NH_2$.

The terms "halogen" or "halo," as used herein, refer to chlorine, bromine, fluorine or iodine.

The compounds of the present invention can also be solvated, especially hydrated. Hydration can occur, for example, during manufacturing of the compounds or compositions comprising the compounds, or the hydration can occur, for example, over time due to the hygroscopic nature of the compounds. The skilled artisan will understand that the phrase "compound of Formula I," as used herein, is meant to include solvated compounds of Formula I.

The term "therapeutically effective amount," as used herein, refers to the amount of a compound of the present invention that, when administered to a patient, is effective to at least partially treat a condition from which the patient is suffering or is suspected to suffer.

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts" refers to salts that are pharmaceutically acceptable and have the desired pharmacological properties. Such salts include, for example, salts that can be formed where acidic protons present in the compounds are capable of reacting with inorganic or organic bases. Suitable inorganic salts include, for example, those formed with the alkali metals or alkaline earth metals, e.g. sodium and potassium, magnesium, calcium, and aluminum. Suitable organic salts include, for example, those formed with organic bases such as the amine bases, e.g. ethanolamine, diethanolamine, triethanolamine, tromethamine, N-methylglucamine, and the like. Pharmaceutically acceptable salts can also include acid addition salts formed from the reaction of amine moieties in the parent compound with inorganic acids and organic acids including the alkane- and arene-sulfonic acids (e.g. acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable organic and inorganic acids).

The terms "inhibitor," "activator," and "modulator" as used in connection with expression or activity refer to inhibitory, activating, or modulating molecules, respectively. Inhibitors of the present invention include compounds or compositions that inhibit expression of PARP or bind to, partially or totally block stimulation, decrease, prevent, delay activation, inactivate, desensitize, or down regulate the activity of PARP. Samples or assays comprising PARP can be treated with a composition of the present invention and compared to control samples without a composition of the present invention. Control samples (untreated with compositions of the present invention) can be assigned a relative activity value of 100%. In certain embodiments, inhibition of PARP is achieved when the activity value relative to the control is about 80% or less.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the compound.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and formulations of the present invention.

The terms "administer," "administering," or "administration," as used herein, refer to either directly administering a compound or composition to a patient, or administering a prodrug derivative or analog of the compound to the patient, which will form an equivalent amount of the active compound or substance within the patient's body.

The terms "treat" and "treating," as used herein, refer to partially or completely alleviating, inhibiting, preventing, ameliorating and/or relieving a condition from which a patient is suspected to suffer.

The terms "suffer" and "suffering," as used herein, refer to one or more conditions with which a patient has been diagnosed, or is suspected to have.

In certain aspects, the present invention is directed to compounds of Formula I:

$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl, wherein the alkyl, alkenyl and rings of the cycloalkyl, phenyl and benzyl groups are optionally substituted with one or more groups (e.g. 1 to 3, 1 to 2 or 1) independently selected from hydroxy, $C_1$-$C_4$ alkoxy, —$CO_2H$, $C_1$-$C_6$ alkoxycarbonyl, $NH_2$, $C_1$-$C_6$ mono- or dialkylamino, or halogen; or $R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms independently selected from N, O, or S, the remainder of the ring atoms being carbon atoms;

$R^7$ is hydrogen, halogen, hydroxy, $NH_2$, $C_1$-$C_3$ alkyl, $C_1$-$C_3$ alkoxy or $NO_2$;

$R^8$ is $C_1$-$C_6$ alkyl, $C_2$-$C_6$ alkenyl, or $C_3$-$C_7$ cycloalkyl wherein the alkyl, alkenyl, and rings of the cycloalkyl are optionally substituted with one or more groups (e.g. 1 to 3, 1 to 2 or 1) independently selected from hydroxy, $C_1$-$C_4$ alkoxy, —$CO_2H$, $C_1$-$C_6$ alkoxycarbonyl, $NH_2$, $C_1$-$C_6$ mono- or dialkylamino, or halogen;

or a pharmaceutically acceptable salt or zwitterionic form thereof.

In certain embodiments $R^1$, $R^2$, $R^3$, and $R^4$ are independently hydrogen, halogen, hydroxyl, $NH_2$, $C_1$-$C_6$ alkoxy, CN, or $C_1$-$C_6$ perfluroalkyl, provided that $R^1$ is not hydrogen. $R^3$ may suitably be hydrogen or halogen. In certain embodiments $R^3$ is hydrogen.

In certain embodiments $R^5$ and $R^6$ are each independently hydrogen, $C_1$-$C_6$ alkyl, $C_2$-$C_4$ alkenyl, $C_3$-$C_7$ cycloalkyl, phenyl or benzyl.

Suitably one or both or $R^5$ and $R^6$ may be $C_1$-$C_6$ alkyl which may be the same or different.

In certain embodiments X is $C_1$-$C_3$ alkylene $C_2$-$C_3$ alkenylene or $C_2$-$C_3$ alkynylene.

When $R^5$ and $R^6$ form a ring together with the nitrogen to which they are attached the ring may suitably be piperidine, morpholine, pyrrolidine, homopiperidine, aziridine or azetidine.

Such substituted thienyl- and furanyl-isoquinolinones acids include the following compounds of Formulas II, III, and IV:

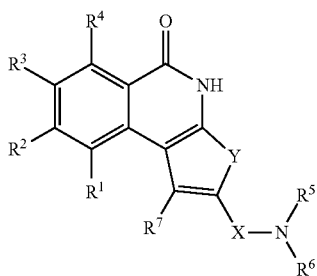

Formula I

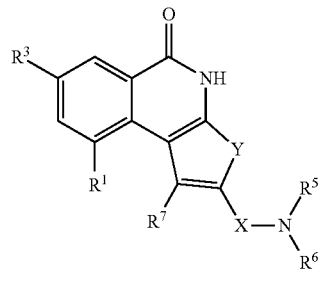

Formula II

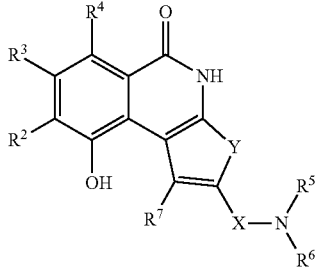

Formula III

Formula I
wherein:
X is $C_1$-$C_9$ alkylene, $C_2$-$C_9$ alkenylene, or $C_2$-$C_9$ alkynylene;
Y is S or O;
$R^1$ is halogen, hydroxy, $NH_2$, $C_1$-$C_6$ alkoxy, CN, or $C_1$-$C_6$ perfluoroalkyl;
$R^2$, $R^3$, and $R^4$ are independently selected from hydrogen, $C_1$-$C_6$ alkyl, halogen, hydroxy, $NH_2$, CN, $C_1$-$C_6$ perfluoroalkyl, $CO_2H$, $OR^8$, $COOR^8$, or $NHR^8$;

Formula IV

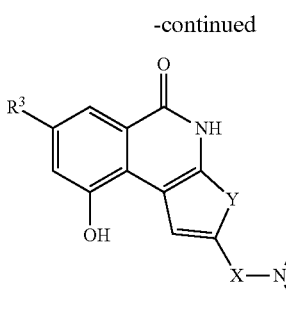

wherein X, Y, $R^1$, $R^2$, $R^3$, $R^4$, $R^5$, $R^6$ and $R^7$ are as defined herein; or a pharmaceutically acceptable salt for thereof.

Compounds of Formulas I, II, III, or IV include those in which:
X is $C_1$-$C_9$ alkylene, $C_2$-$C_9$ alkenylene, or $C_2$-$C_9$ alkynylene;
Y is S or O;
$R^1$ is halogen, hydroxy, $NH_2$, $C_1$-$C_6$ alkoxy, CN, or $C_1$-$C_6$ perfluoroalkyl;
$R^2$, $R^3$, and $R^4$ are independently hydrogen, halogen, hydroxy, $NH_2$, $C_1$-$C_6$ alkoxy, CN, or $C_1$-$C_6$ perfluoroalkyl;
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or
$R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; and
$R^7$ is hydrogen, halogen, hydroxy, $NH_2$, $C_1$-$C_3$ alkyl, $C_1$-$C_3$ alkoxy or $NO_2$; or a pharmaceutically acceptable salt form thereof.

Compounds of Formulas I, II, III, or IV further include those in which:
X is $C_1$-$C_3$ alkylene, $C_2$-$C_3$ alkenylene, or $C_2$-$C_3$ alkynylene;
Y is S or O;
$R^1$ is halogen, hydroxy, $NH_2$, $C_1$-$C_6$ alkoxy, CN, or $C_1$-$C_6$ perfluoroalkyl;
$R^2$, $R^3$, and $R^4$ are independently hydrogen, halogen, hydroxy, $NH_2$, $C_1$-$C_6$ alkoxy, CN, or $C_1$-$C_6$ perfluoroalkyl;
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or
$R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; and
$R^7$ is hydrogen; or a pharmaceutically acceptable salt or zwitterionic form thereof.

Compounds of Formulas I, II, III, or IV further include those in which:
$R^1$ is halogen, hydroxy, $NH_2$, $C_1$-$C_6$ alkoxy, CN, or $C_1$-$C_6$ perfluoroalkyl;
$R^2$ and $R^4$ are independently hydrogen, halogen, hydroxy, $NH_2$, $C_1$-$C_6$ alkoxy, CN, or $C_1$-$C_6$ perfluoroalkyl;
$R^7$ is hydrogen, halogen, hydroxy, $NH_2$, $C_1$-$C_3$ alkyl, $C_1$-$C_3$ alkoxy or $NO_2$; $R^3$ is hydrogen or halogen;
Y is S;
X is $C_1$-$C_9$ alkylene, $C_2$-$C_9$ alkenylene, or $C_2$-$C_9$ alkynylene; and
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or $R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; or a pharmaceutically acceptable salt or zwitterionic form thereof.

Compounds of Formulas I, II, III, or IV include those in which:
$R^1$, $R^2$, $R^4$, and $R^7$ are as defined herein;
$R^3$ is hydrogen or halogen;
Y is O;
X is $C_1$-$C_9$ alkylene, $C_2$-$C_9$ alkenylene, or $C_2$-$C_9$ alkynylene; and
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or $R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen;
Y is S;
X is $C_1$-$C_9$ alkylene, $C_2$-$C_9$ alkenylene, or $C_2$-$C_9$ alkynylene; and
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or $R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen;
Y is O;
X is $C_1$-$C_9$ alkylene, $C_2$-$C_9$ alkenylene, or $C_2$-$C_9$ alkynylene; and
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or $R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen, halogen, hydroxy, $NH_2$, $C_1$-$C_6$ alkoxy, CN, or $C_1$-$C_6$ perfluoroalkyl;
Y is S;
X is $C_1$-$C_9$ alkylene, $C_2$-$C_9$ alkenylene, or $C_2$-$C_9$ alkynylene; and
$R^5$ and $R^6$ are each, independently, $C_1$-$C_6$ alkyl; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen, halogen, hydroxy, $NH_2$, $C_1$-$C_6$ alkoxy, CN, or $C_1$-$C_6$ perfluoroalkyl;
Y is O;
X is $C_1$-$C_9$ alkylene, $C_2$-$C_9$ alkenylene, or $C_2$-$C_9$ alkynylene; and
$R^5$ and $R^6$ are each, independently, $C_1$-$C_6$ alkyl; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen or halogen;
Y is S;
X is $C_1$-$C_9$ alkylene, $C_2$-$C_9$ alkenylene, or $C_2$-$C_9$ alkynylene; and
$R^5$ and $R^6$ are each, independently, $C_1$-$C_6$ alkyl; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen or halogen;
Y is O;
X is $C_1$-$C_9$ alkylene, $C_2$-$C_9$ alkenylene, or $C_2$-$C_9$ alkynylene; and
$R^5$ and $R^6$ are each, independently, $C_1$-$C_6$ alkyl; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen;
Y is S;
X is $C_1$-$C_9$ alkylene, $C_2$-$C_9$ alkenylene, or $C_2$-$C_9$ alkynylene and
$R^5$ and $R^6$ are each, independently, $C_1$-$C_6$ alkyl; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen;
Y is O;
X is $C_1$-$C_9$ alkylene, $C_2$-$C_9$ alkenylene, or $C_2$-$C_9$ alkynylene; and
$R^5$ and $R^6$ are each, independently, $C_1$-$C_6$ alkyl; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen or halogen;
Y is S;
X is $C_1$-$C_9$ alkylene, $C_2$-$C_9$ alkenylene, or $C_2$-$C_9$ alkynylene; and
$R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms. In certain aspects, the heterocyclic ring is piperidine, morpholine, pyrrolidine, homopiperidine, aziridine, or azetidine; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen or halogen;
Y is O;
X is $C_1$-$C_9$ alkylene, $C_2$-$C_9$ alkenylene, or $C_2$-$C_9$ alkynylene; and
$R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms. In certain aspects, the heterocyclic ring is piperidine, morpholine, pyrrolidine, homopiperidine, aziridine, or azetidine; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen;
Y is S;
X is $C_1$-$C_9$ alkylene, $C_2$-$C_9$ alkenylene, or $C_2$-$C_9$ alkynylene; and
$R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; or a pharmaceutically acceptable salt or zwitterionic form thereof. In certain aspects, the heterocyclic ring is piperidine, morpholine, pyrrolidine, homopiperidine, aziridine, or azetidine.

Compounds of Formulas I, II, III, or IV further include those in which:
$R^1$, $R^2$, $R^4$, $R^7$, and $R^8$ are as defined herein;
$R^3$ is hydrogen;
Y is O;
X is $C_1$-$C_9$ alkylene, $C_2$-$C_9$ alkenylene, or $C_2$-$C_9$ alkynylene; and
$R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; or a pharmaceutically acceptable salt or zwitterionic form thereof. In certain aspects, the heterocyclic ring is piperidine, morpholine, pyrrolidine, homopiperidine, aziridine, or azetidine.

Compounds of Formulas I, II, III, or IV further include those in which:
$R^1$, $R^2$, $R^4$, $R^7$, and $R^8$ are as defined herein;
$R^3$ is hydrogen, halogen, hydroxy, $NH_2$, $C_1$-$C_6$ alkoxy, CN, or $C_1$-$C_6$ perfluoroalkyl;
Y is S;
X is $C_1$-$C_3$ alkylene; and
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or $R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen, halogen, hydroxy, $NH_2$, $C_1$-$C_6$ alkoxy, CN, or $C_1$-$C_6$ perfluoroalkyl;
Y is O;
X is $C_1$-$C_3$ alkylene; and $R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or $R^5$ and $R^6$ together with the nitrogen to which they are attached form a saturated, partially unsaturated, or unsaturated 3 to 12 membered monocytic or bicyclic heterocyclic ring optionally comprising from one to three additional ring heteroatoms selected from N, O, or S, the remainder of the ring atoms being carbon atoms; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen or halogen or $R^3$ is hydrogen;
Y is S;
X is $C_1$-$C_3$ alkylene; and
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or $R^5$ and $R^6$ together with the nitrogen to which they are attached form a saturated, partially unsaturated, or unsaturated 3 to 12 membered monocytic or bicyclic heterocyclic ring optionally comprising from one to three additional ring heteroatoms selected from N, O, or S, the remainder of the ring atoms being carbon atoms; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen or halogen or $R^3$ is hydrogen;
Y is O;
X is $C_1$-$C_3$ alkylene; and
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or $R^5$ and $R^6$ together with the nitrogen to which they are attached form a saturated, partially unsaturated, or unsaturated 3 to 12 membered monocytic or bicyclic heterocyclic ring optionally comprising from one to three additional ring heteroatoms selected from N, O, or S, the remainder of the ring atoms being carbon atoms; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen or halogen;
Y is S;
X is $C_1$-$C_3$ alkylene; and
$R^5$ and $R^6$ are each, independently, $C_1$-$C_6$ alkyl; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen or halogen;
Y is O;
X is $C_1$-$C_3$ alkylene; and
$R^5$ and $R^6$ are each, independently, $C_1$-$C_6$ alkyl; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen;
Y is S;
X is $C_1$-$C_3$ alkylene; and
$R^5$ and $R^6$ are each, independently, $C_1$-$C_6$ alkyl; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen;

Y is O;
X is $C_1$-$C_3$ alkylene; and
$R^5$ and $R^6$ are each, independently, $C_1$-$C_6$ alkyl; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen;
Y is S;
X is methyl; and
$R^5$ and $R^6$ are each, independently, $C_1$-$C_6$ alkyl; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen;
Y is O;
X is methyl; and
$R^5$ and $R^6$ are each, independently, $C_1$-$C_6$ alkyl; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen;
Y is S;
X is methyl; and
$R^5$ and $R^6$ are each, independently methyl; or a pharmaceutically acceptable salt or zwitterionic form thereof.

Compounds of Formulas I, II, III, or IV further include those in which:
$R^1$, $R^2$, $R^4$, $R^7$, and $R^8$ are as defined herein;
$R^3$ is hydrogen;
Y is O;
X is methyl; and
$R^5$ and $R^6$ are each, independently methyl; or a pharmaceutically acceptable salt or zwitterionic form thereof.

Compounds of Formulas I, II, III, IV, V, or VI further include those in which:
$R^1$ is halogen, hydroxy, $NH_2$, methoxy, CN, or $CF_3$; and
$R^2$ is hydrogen, halogen, hydroxy, $NH_2$, methoxy, CN, or $CF_3$.

In exemplary embodiments, halogen is fluorine.
In exemplary embodiments, X is $C_1$-$C_3$ alkylene, $C_2$-$C_3$ alkenylene, or $C_2$-$C_3$ alkynylene.

Compounds of Formula I include:
2-dimethylaminomethyl-9-methoxythieno[2,3-c]isoquinolin-5(4H)-one;
8-chloro-2-[(dimethylamino)methyl]thieno[2,3-c]isoquinolin-5(4H)-one;
2-[(dimethylamino)methyl]-8-methoxythieno[2,3-c]isoquinolin-5(4H)-one;
2-dimethylaminomethyl-9-hydroxythieno[2,3-c]isoquinolin-5(4H)-one;
2-[(dimethylamino)methyl]-7-fluoro-9-hydroxythieno[2,3-c]isoquinolin-5(4H)-one;
2-[(dimethylamino)methyl]-7-fluorothieno[2,3-c]isoquinolin-5(4H)-one;
2-[(dimethylamino)methyl]-9-fluorothieno[2,3-c]isoquinolin-5(4H)-one;
2-[(dimethylamino)methyl]furo[2,3-c]isoquinolin-5(4H)-one hydrochloride;
9-hydroxy-2-(morpholin-4-ylmethyl)thieno[2,3-c]isoquinolin-5(4H)-one;
9-hydroxy-2-(piperidin-1-ylmethyl)thieno[2,3-c]isoquinolin-5(4H)-one;
9-hydroxy-2-(1,3-thiazolidin-3-ylmethyl)thieno[2,3-c]isoquinolin-5(4H)-one;

9-hydroxy-2-{[(1-methylethyl)amino]methyl}thieno[2,3-c]isoquinolin-5(4H)-one;

9-hydroxy-2-(pyrrolidin-1-ylmethyl)thieno[2,3-c]isoquinolin-5(4H)-one;

2-[(4-bromopiperidin-1-yl)methyl]-9-hydroxythieno[2,3-c]isoquinolin-5(4H)-one;

2-[(dibenzylamino)methyl]-9-hydroxythieno[2,3-c]isoquinolin-5(4H)-one;

2-{[benzyl(methyl)amino]methyl}-9-hydroxythieno[2,3-c]isoquinolin-5(4H)-one;

or pharmaceutically acceptable salt or zwitterionic forms thereof.

In certain embodiments, the pharmaceutically acceptable salt of a compound of Formula I is a hydrochloride or hydrobromide salt.

Compounds of Formula I further include 2-dimethylaminomethyl-9-hydroxythieno[2,3-c]isoquinolin-5(4H)-one or a pharmaceutically acceptable salt or zwitterionic form thereof.

Compounds of Formula I further include amorphous 2-dimethylaminomethyl-9-hydroxythieno[2,3-c]isoquinolin-5(4H)-one or a pharmaceutically acceptable salt or zwitterionic form thereof.

Compounds of Formula I further include 2-dimethylaminomethyl-9-hydroxythieno[2,3-c]isoquinolin-5(4H)-one hydrate.

Compounds of Formula I further include 2-dimethylaminomethyl-9-hydroxythieno[2,3-c]isoquinolin-5(4H)-one monohydrate.

Compounds of Formula I further include 2-dimethylaminomethyl-9-hydroxythieno[2,3-c]isoquinolin-5(4H)-one monohydrate having an endotherm at about 139° C.

Compounds of Formula I further include 2-dimethylaminomethyl-9-hydroxythieno[2,3-c]isoquinolin-5(4H)-one anhydrate.

Compounds of Formula I further include a zwitterion of 2-dimethylaminomethyl-9-hydroxythieno[2,3-c]isoquinolin-5(4H)-one.

Compounds of Formula I further include 2-dimethylaminomethyl-9-hydroxythieno[2,3-c]isoquinolin-5(4H)-one anhydrate having endotherms at about 210° C. and 270° C.

Compounds of Formula I further include a crystalline anhydrous form of 2-dimethylaminomethyl-9-hydroxythieno[2,3-c]isoquinolin-5(4H)-one having at least 3 characteristic 2θ values measured using CuKα radiation selected from 10.4, 10.6, 14.5, 21.3, 26.8 and 32.1.

Compounds of Formula I further include a crystalline monohydrate form of 2-dimethylaminomethyl-9-hydroxythieno[2,3-c]isoquinolin-5(4H)-one having at least 3 characteristic 2θ values measured using CuKα radiation selected from 8.3, 8.6, 11.7, 18.4, 18.9, 19.4, 25.7 and 28.7.

Compounds of Formula I further include a crystalline anhydrous form of 2-dimethylaminomethyl-9-hydroxythieno[2,3-c]isoquinolin-5(4H)-one with an average particle size of about 5 to 10 μm and more particularly about 7 μm.

Compounds of Formula I further include a crystalline anhydrous form of 2-dimethylaminomethyl-9-hydroxythieno[2,3-c]isoquinolin-5(4H)-one characterized by orthorhombic agglomerations with an average length of about 5 to 10 μm and more particularly about 6

In some embodiments, compounds of the present invention can be used to modulate the activity of PARP. Such compounds are of interest for the treatment of a variety of disease and conditions. In certain embodiments, they can be administered to a subject for the treatment of tissue damage, apoptotic and/or necrotic cell death due to ischemia and reperfusion arising from various neurological diseases such as, for example, stroke, cerebral or spinal trauma, epileptic events, cerebral damage due to cardiac arrest and/or to situations of prolonged hypotension, respiratory arrest, carbon monoxide or cyanide poisoning, drowning or hydrocephalus. The cerebral insult can also be of a toxic nature (excitotoxins and other chemical products), iatrogenic (including surgical) and due to ionizing radiation. Tissue damage due to ischemia and reperfusion can also affect the myocardium and be present in many cardiopathies such as post-infarction, during and after coronary by-pass surgery, on the resumption of perfusion in transplanted hearts and indeed any time when for surgical reasons cardiac arrest is performed, and blood reperfusion is initiated. The kidney, the liver, the intestine and skeletal musculature are susceptible to damage due to ischemia and reperfusion. This can occur in septic, endotoxic, hemorrhagic and compression shock. It also occurs in strangulated hernia, strangulation of intestinal loops, and after prolonged compression of joints in multiply traumatized patients.

In some embodiments, compounds of the present invention can be administered to a subject for the treatment of degenerative diseases. The inhibition of PARP can extend the reproductive capacity of various cells and be utilized to prevent diseases typically associated with aging. Exemplary degenerative diseases include those of the central nervous system such as, for example, Parkinson's disease, Alzheimer's dementia, Huntington's chorea, amyotrophic lateral sclerosis, macular degeneration and retinal ischemia. Other degenerative diseases include, for example, the aging of the skin, degenerative diseases of the muscles (muscular dystrophy), bones (osteoporosis) and vascular system (atherosclerosis), diabetes, and diseases of the immune system present during senescence.

In some embodiments, compounds of the present invention can be administered to a subject for the treatment of inflammatory diseases. Excessive activation of PARP can be harmful in various diseases of predominantly inflammatory nature, both of the central nervous system and of peripheral organs. Compounds of the invention can thus be useful in the following pathological situations: multiple sclerosis and other demyelinizing diseases, Guillain-Barre syndrome, neuralgias of the trigeminus and/or other cranial nerves, peripheral neuropathies and other chronic pain, osteoarthritis, and inflammatory diseases of the intestine (Crohn's disease, ulcerative colitis, and other forms of colitis).

In some embodiments, compounds of the present invention can be administered to a subject for the treatment of tumor diseases. PARP inhibitors can facilitate the death of tumor cells induced by ionizing agents or by chemotherapeutic agents and can be used, both alone and in combination with other treatments, in the prevention and in the therapy of various forms of cancer, for example, leukemia and/or sarcoma, whether these are primary or associated with AIDS, breast cancer, refractory solid tumors, lymphoid malignancies, brain tumors, and p53 deficient tumors. The PARP inhibitors can act to enhance the cytotoxicity of antitumor agents. For example, PARP inhibitors can act to enhance the cytotoxicity of topoisomerase I and II inhibitors, and alkylating agents including, for example, temozolomide.

In some embodiments, compounds of the present invention can be administered to a subject for the treatment of cancers, including, for example, cancers of the female reproductive organs including, for example, ovarian cancer, cervical cancer and uterine cancer; lung cancer; breast cancer; renal cell carcinoma; Hodgkin's lymphoma; Non-Hodgkin's lymphoma; cancers of the genitourinary system including, for example, kidney cancer, prostate cancer, bladder cancer, and urethral cancer; cancers of the head and neck; liver cancer; cancers of the gastrointestinal system including, for example, stomach cancer, esophageal cancer, small bowel cancer or colon cancer; cancers of the biliary tree; pancreatic cancer; cancers of the male reproductive system including, for example, testicular cancer; Gestational trophoblastic disease; cancers of the endocrine system including, for example, thyroid cancer, parathyroid cancer, adrenal gland cancer, carcinoid tumors, insulinomas and PNET tumors; sarcomas, including, for example, Ewing's sarcoma, osteosarcoma, liposarcoma, leiomyosarcoma, and rhabdomyosarcoma; mesotheliomas; cancers of the skin; melanomas; cancers of the central nervous system; pediatric cancers; and cancers of the hematopoietic system including, for example, all forms of leukemia, myelodysplastic syndromes, myeloproliferative disorders and multiple myeloma.

In some embodiments, compounds of the present invention can be administered to a subject for the treatment of bone fractures as well as bone disorders, including osteoporosis, and for the treatment of arthritis, chronic obstructive pulmonary disease, cartilage defects, leiomyoma, acute myeloid leukemia, wound healing, prostate cancer, autoimmune inflammatory disorders, such as Graves ophthalmopathy, and combinations thereof.

In some embodiments, compounds of the present invention can be administered to a subject for the treatment of retinal degeneration and axotomy.

In some embodiments, compounds of the present invention can be administered to a subject for the treatment of cardiovascular dysfunction, including myocardial infarction and atherosclerosis.

In certain embodiments, compounds of the present invention are administered to a subject following a partial or complete artery occlusion in order to reduce brain damage. The compounds can be administered immediately after the occlusion or even with a significant delay after artery occlusion. For example, in certain embodiments, administration will start 1 to 10 hours (i.e., 1, 2, 3, 4, 5, 6, 7, 8, 9, or 10 hours) after artery occlusion, preferably 1 to 4 hours after artery occlusion.

In certain embodiments, the present invention therefore provides methods of treating, preventing, inhibiting, or alleviating each of the maladies listed above in a mammal, preferably in a human, comprising administering a therapeutically effective amount of a compound of the present invention to a patient suspected to suffer from such a malady.

In certain embodiments, the invention relates to compositions comprising at least one compound of the present invention or pharmaceutically acceptable salt thereof, and one or more pharmaceutically acceptable carriers, excipients, or diluents. In certain embodiments, the compositions comprise mixtures of one or more compounds of the present invention.

In other embodiments of the present invention, compounds of the present invention may be administered together with or in combination with a thrombolytic agent such as tissue plasminogen activator or tPA for instance as an adjunctive treatment of ischemic stroke.

Certain of the compounds of the present invention contain stereogenic carbon atoms or other chiral elements and thus give rise to stereoisomers, including enantiomers and diastereomers. The invention generally relates to all stereoisomers of the compounds of Formula I, as well as to mixtures of the stereoisomers. Throughout this application, the name of a compound without indication as to the absolute configuration of an asymmetric center is intended to embrace the individual stereoisomers as well as mixtures of stereoisomers. Reference to optical rotation [(+), (−) and (±)] is utilized to distinguish the enantiomers from one another and from the racemate. Furthermore, throughout this application, the designations R* and S* are used to indicate relative stereochemistry, employing the Chemical Abstracts convention which automatically assigns R* to the lowest numbered asymmetric center.

An enantiomer can, in some embodiments of the invention, be provided substantially free of the corresponding enantiomer. Thus, reference to an enantiomer as being substantially free of the corresponding enantiomer indicates that it is isolated or separated via separation techniques or prepared so as to be substantially free of the corresponding enantiomer. "Substantially free," as used herein, means that a significantly lesser proportion of the corresponding enantiomer is present. In preferred embodiments, less than about 90% by weight of the corresponding enantiomer is present relative to desired enantiomer, more preferably less than about 1% by weight. Preferred enantiomers can be isolated from racemic mixtures by any method known to those skilled in the art, including high performance liquid chromatography (HPLC), and the formation and crystallization of chiral salts, or preferred enantiomers, can be prepared by methods described herein. Methods for the preparation of enantiomers are described, for example, in Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972), each of which is hereby incorporated by reference in its entirety.

When compounds of the present invention are zwitterions, it will be appreciated that there is an equilibrium between the compounds of the invention in their zwitterionic form and their non-ionic form. The zwitterionic and non-ionic forms and equilibrium mixtures of zwitterionic and non-ionic forms are all within the scope of the invention.

Compounds of the present invention may be deuterated such that one or more hydrogens may be replaced by a heavy isotope thereof. Deuterated compounds contain no less than 1%, 5%, 10%, or 50% deuterium at a given location. Deuterium can be incorporated to different positions according to synthetic procedures by using appropriate dueterated intermediates which are available commercially or prepared by methods known to those skilled in the art. Deuterium can also be incorporated to various positions having an exchangeable proton, such as hydroxyl or amide via proton-deuterium equilibrium exchange.

Compounds of the present invention may be tautomers. Tautomer refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The following synthetic schemes are designed to illustrate, but not limit, general procedures for the preparation of compounds of the present invention. The reagents used can be either commercially obtained or can be prepared by standard procedures described in the literature. It is intended that the scope of this invention will cover all isomers (enantiomeric and diastereomeric) and all mixtures, including but not limited to racemic mixtures. The isomeric forms of the compounds of this invention may be separated or resolved using methods known to those skilled in the art or by synthetic methods that are stereospecific or asymmetric.

As illustrated in Scheme 1, compounds of the present invention can be prepared from 2,3-dibromofuran. Commercially available 2,3-dibromofuran (II) is treated with n-BuLi in Et$_2$O followed by trapping of the resulting anion with reagents such as DMF or N-formylpiperidine to give the corresponding 2-formyl-3-bromofuran (III) according to Tietze, L. F., et al., *Synlett*, 2002, 2083-2085. Protection of the formyl group with a diol such as ethylene glycol in the presence of p-TsOH.H$_2$O gives acetal (IV). Treatment of this acetal with n-BuLi followed by quenching with B(On-Bu)$_3$ produces boronic acid (V). Suzuki cross-coupling with aryl bromides followed by acetal hydrolysis gives the corresponding 2-formyl-3-arylated thiophene (VI). Oxidation of the aldehyde with reagents such as the Jones reagent produces the corresponding acid Tricycle formation (VIII) is accomplished by converting the carboxylic acid to the corresponding acid chloride using reagents such as SOCl$_2$ or (CO)$_2$Cl$_2$, conversion to the acyl azide using sodium azide which undergoes Curtius rearrangement to give the corresponding isocyanate, followed by closure under heating in high boiling non-polar solvents such as dichlorobenzene. Compounds (I) are then prepared by adding the amine side chain under Mannich conditions (amine, CH$_2$O, heating).

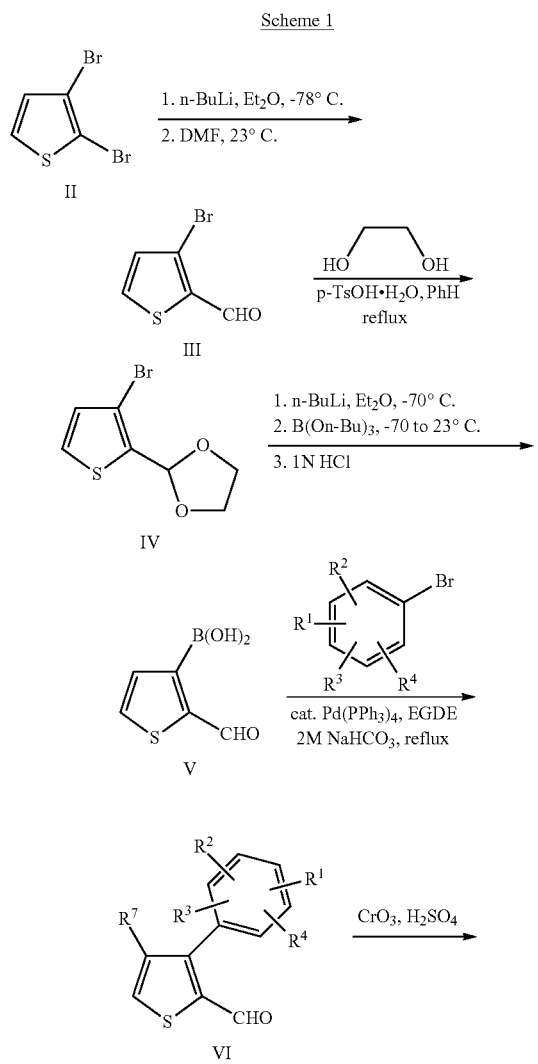

Scheme 1

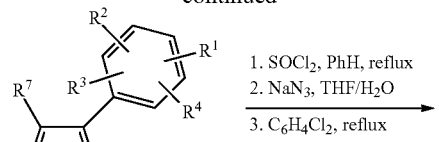

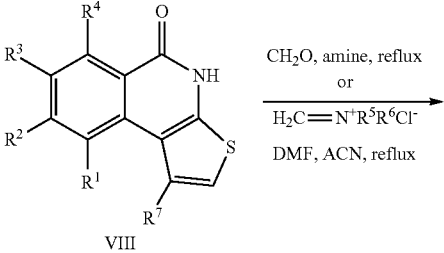

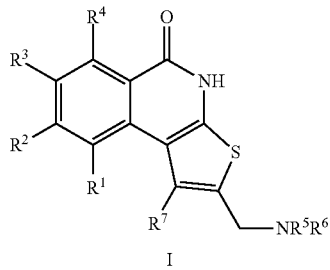

The preparation of furanic acid (XI) is undertaken according to Scheme 2. Furan bromide (X) is coupled with aryl boronic acid in the presence of Pd(Ph$_3$P)$_4$, aqueous Na$_2$CO$_3$ in DME to produce (XI). Furan (IX) analogs of I can then be prepared as in Scheme 1. Tricycle formation is accomplished by converting the carboxylic acid to the corresponding acid chloride using reagents such as SOCl$_2$ or (CO)$_2$Cl$_2$, conversion to the acyl azide using sodium azide which undergoes Curtius rearrangement to give the corresponding isocyanate, followed by closure under heating in high boiling non-polar solvents such as dichlorobenzene. Compound (IX) is then prepared by adding the amine side chain under Mannich conditions (amine, CH$_2$O, heating).

Scheme 2

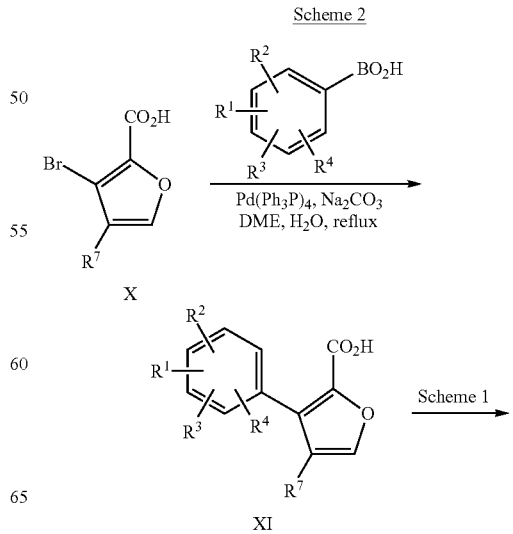

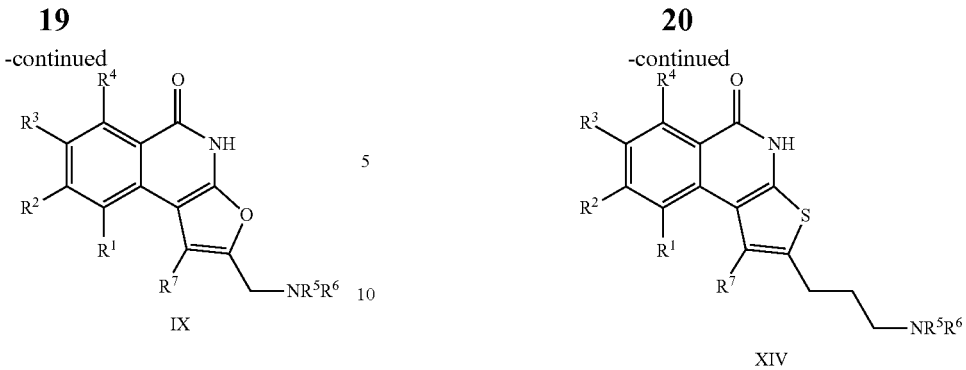

The preparation of alkyne analogs (XIII) and propylamine analogs (XIV) is shown in Scheme 3. Thiophenes (VIII) can be iodinated selectively using an electrophilic iodine source such as ICl to give the corresponding 2-iodothiophenes (XII). Sonogashira cross-coupling using propargyl amines in the presence of catalytic Pd(II) and CuI gives the corresponding thiophene-alkynes (XIII). The corresponding propyl analogs (XIV) are prepared by reduction using $H_2$ and Pd on carbon. Alkene derivatives (XV) are prepared according to Scheme 4. Iodinated analog (XII) undergoes Heck Pd-catalyzed coupling with allyl amines to produce alkene compounds (XV).

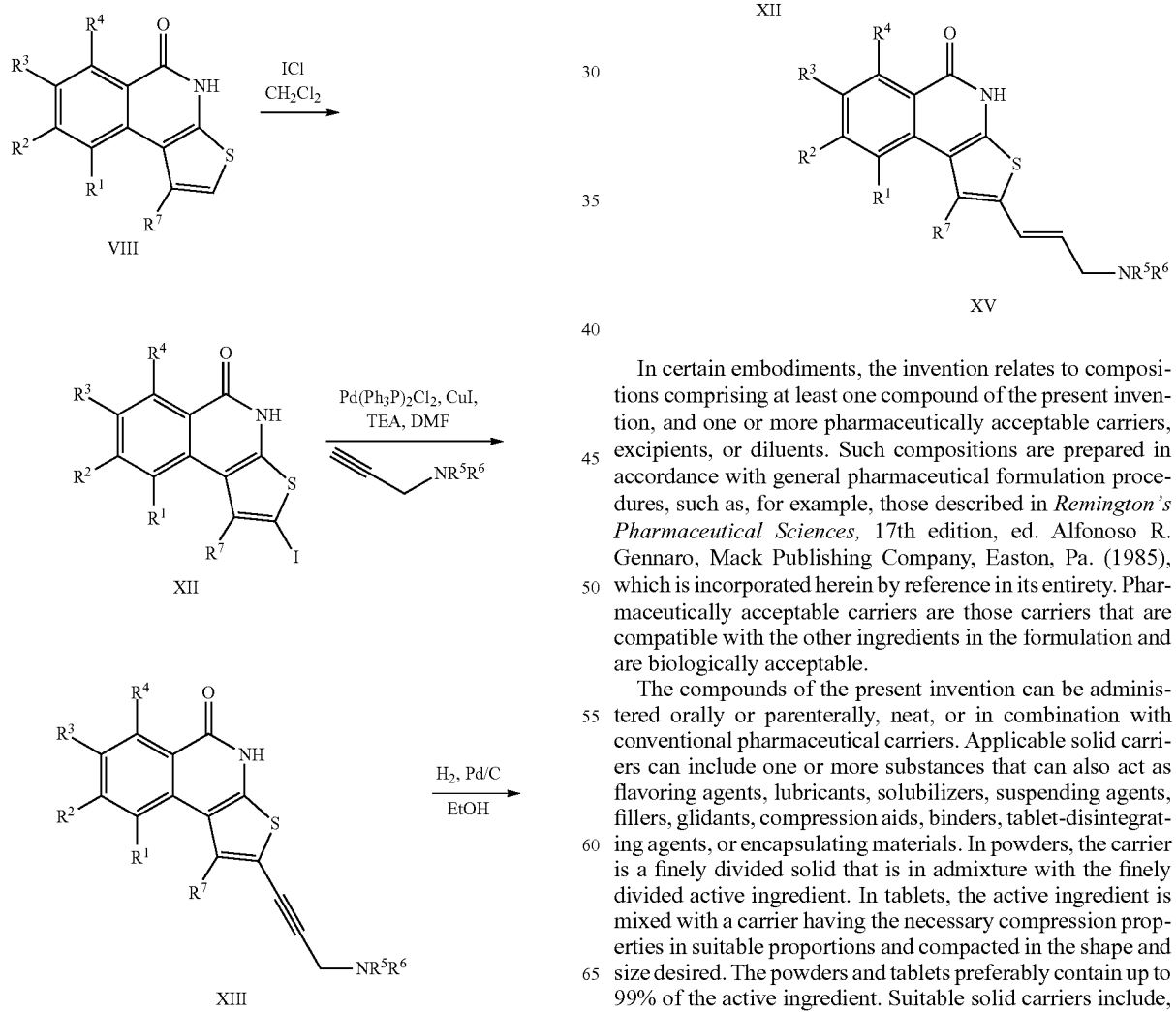

In certain embodiments, the invention relates to compositions comprising at least one compound of the present invention, and one or more pharmaceutically acceptable carriers, excipients, or diluents. Such compositions are prepared in accordance with general pharmaceutical formulation procedures, such as, for example, those described in *Remington's Pharmaceutical Sciences,* 17th edition, ed. Alfonoso R. Gennaro, Mack Publishing Company, Easton, Pa. (1985), which is incorporated herein by reference in its entirety. Pharmaceutically acceptable carriers are those carriers that are compatible with the other ingredients in the formulation and are biologically acceptable.

The compounds of the present invention can be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be administered by, for example, intramuscular, intraperitoneal or subcutaneous injection. Sterile solutions can also be administered intravenously such as by an IV push, bolus, or infusion or a combination thereof. Compositions for oral administration can be in either liquid or solid form.

The compounds of the present invention can be administered rectally or vaginally in the form of a conventional suppository. For administration by intranasal or intrabronchial inhalation or insufflation, the compounds can be formulated into an aqueous or partially aqueous solution, which can then be utilized in the form of an aerosol. The compounds of the present invention can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition can be sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration and the state of the patient, the manner of administration, and the like. In therapeutic applications, compounds of Formula I can be provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age, and response pattern of the patient. The compounds can be administered orally, rectally, parenterally, or topically to the skin and mucosa. The usual daily dose depends on the specific compound, method of treatment and condition treated. The usual daily dose is, for example, from 0.01-1000 mg/kg for oral application, preferably 0.5-500 mg/kg, either in a single dose or in subdivided doses, for example from one to three times daily and from about 0.1-100 mg/kg for parenteral application, preferably 0.5-50 mg/kg, from one to three times daily.

In certain embodiments, the present invention is directed to prodrugs of compounds provided herein. The term "prodrug," as used herein, means a compound that is convertible in vivo by metabolic means (e.g. by hydrolysis) to a compound of Formula I. Various forms of prodrugs are known in the art such as those discussed in, for example, Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "*Design and Application of Prodrugs, Textbook of Drug Design and Development*, Chapter 5, 113-191 (1991), Bundgaard, et al., *Journal of Drug Delivery Reviews,* 8:1-38(1992), Bundgaard, *J. of Pharmaceutical Sciences,* 77:285 et seq. (1988); and Higuchi and Stella (eds.) *Prodrugs as Novel Drug Delivery Systems*, American Chemical Society (1975), each of which is hereby incorporated by reference in its entirety.

EXAMPLES

The following examples are illustrative of certain embodiments of the invention and should not be considered to limit the scope of the invention. The reagents used can be either commercially obtained or can be prepared by standard procedures described in the literature. It is intended that the scope of this invention will cover all isomers (enantiomeric and diastereomeric) and all mixtures, including but not limited to racemic mixtures. The isomeric forms of the compounds of this invention may be separated or resolved using methods known to those skilled in the art or by synthetic methods that are stereospecific or asymmetric.

Example 1

2-Dimethylaminomethyl-9-methoxythieno[2,3-c]isoquinolin-5(4H)-one hydrochloride

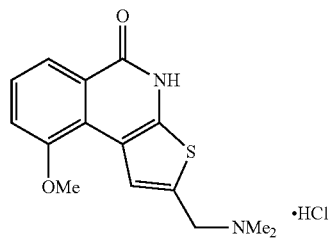 [SMILES: COc1cccc2c(=O)[nH]c3sc(CN(C)C)cc3c12 ; Cl]

9-Methoxythieno[2,3-c]isoquinolin-5(4H)-one (Pellicciari, R., et al., *Farmaco*, 2003, 58, 851-858) (0.20 g, 0.86 mmol), was dissolved in a mixture of dry DMF (1 ml) and dry MeCN (2 ml) and treated with N,N-dimethyl(methylene)ammonium chloride (1.2 mmol) prepared according to a known procedure (Kinast, G. et al. *Angew. Chem. Int. Ed. Engl.* 1976, 15, 239-240. Bohme, H et al. *Chem. Ber.* 1960, 93, 1305). The reaction mixture was refluxed overnight. The formed solid was then filtered and washed with dry diethyl ether to give title compound (83% yield) as a solid. mp 264-265° C.

$^1$H-NMR (DMSO, 400 MHz) δ 2.72 (s, 6H, N(CH$_3$)$_2$), 4.01 (s, 3H, OCH$_3$), 4.51 (s, 2H, CH$_2$N), 7.42 (d J=8.04 Hz, 1H, H-Ph), 7.50 (t J=7.88 Hz, 1H, H-Ph), 7.84 (d J=7.75 Hz, 1H, H-Ph), 8.15 (s, 1H, H-Th), 12.59 (s, 1H, NH).

$^{13}$C-NMR (DMSO, 400 MHz) δ 43.1, 43.1, 56.0, 57.9, 116.0, 116.3, 121.4, 125.3, 127.1, 128.9, 132.4, 144.9, 156.6, 162.6.

MS (ES$^+$) m/z 289 (M+H)

Example 2

2-Dimethylaminomethyl-9-hydroxythieno[2,3-c]isoquinolin-5(4H)-one hydrobromide

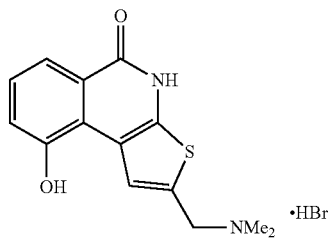 [SMILES: CN(C)Cc1cc2c([nH]c(=O)c3cccc(O)c32)s1 ; Br]

Boron tribromide, 1 M CH$_2$Cl$_2$ solution, (0.1 ml, 0.41 mmol) was added to a solution of 2-dimethylaminomethyl-9-methoxythieno[2,3-c]isoquinolin-5(4H)-one hydrochloride (0.03 g, 0.09 mmol) in dichloromethane (2 ml) and the reaction mixture was refluxed for 24 hours. The mixture was cooled to 23° C., poured on to ice and the resulting mixture was evaporated under reduced pressure. The mixture was purified by crystallization with 96% ethanol to obtain the title compound (54% yield) as pure solid.

mp>300° C.

$^1$H-NMR (DMSO, 400 MHz) δ 2.74 (s, 6H, N(CH$_3$)$_2$), 4.53 (s, 2H, CH$_2$N), 7.26 (dd J=1.24, 7.92, 1H, H-Ph), 7.36 (t J=7.92, 1H, H-Ph), 7.75 (dd J=1.20, 7.88 Hz, 1H, H-Ph), 8.19 (s, 1H, H-Th), 10.61 (s, 1H, OH), 12.44 (s, 1H, NH).

$^{13}$C-NMR (DMSO, 400 MHz) δ 41.7, 54.7, 115.5, 118.4, 118.7, 120.0, 122.5, 125.9, 127.4, 131.0, 142.5, 153.5, 161.3.

MS (ES$^+$) m/z 275 (M+H)

Examples 2A-2D

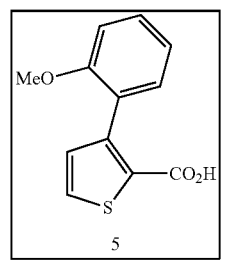

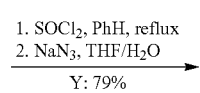

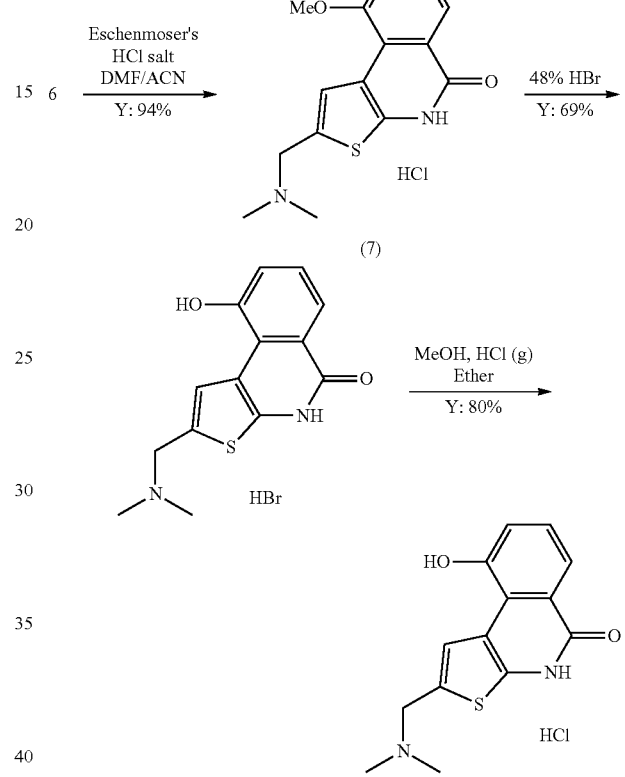

(2A) 9-Methoxy-4H-thieno[2,3-c]isoquinolin-5-one (6)

To a suspension of 3-(2-Methoxy-phenyl)-thiophene-2-carboxylic acid (6 g; 25.61 mmol) in benzene (90 mL) was added SOCl$_2$ (20 mL) and dimethylformamide (DMF) (2 drops). The reaction mixture was heated and reflux for 3 to 4 hours. A worked up TLC and NMR sample showed the reaction was complete. The volatiles were removed under reduced pressure and the residue was taken back in toluene and concentrated to dryness to give the acid chloride intermediate in quantitative yield and proven by an IR and NMR spectroscopy. This was then dissolved in tetrahydrofuran (THF) (90 mL), and cooled to 0° C. A prepared solution of sodium azide (2.5 g, 38.42 mmol) in water (18 mL) was added over 1 minute. The resulting yellow brownish reaction mixture was heated to room temperature and it stirred for 1 hour. A worked up TLC sample showed the reaction was complete.

The reaction mixture was quenched with ice, water and extracted with ether (2 x). Combined ether extracts were dried over MgSO$_4$ filtered off and concentrated to dryness without heat to give the acylazide intermediate (6.3 g as light brownish solid) in 93% yield. The IR and NMR data were consistent. This acylazide intermediate was dissolved in 1, 2, dichlorobenzene (110 mL) and was added drop wise over 1.3 hours to a prepared boiling solution (185° C.) of 1, 2, dichlorobenzene (150 mL). The reaction was complete after 3 to 4 hours as indicated by work up TLC and HPLC samples. The resulting black colored reaction mixture was cooled to room temperature and stirred overnight. Solvent was removed in vacuum and the black residue was triturated with $CH_2Cl_2$ (100 mL), filtered off dried to gave intermediate 6 (9-Methoxy-4H-thieno[2,3-c]isoquinolin-5-one; 4.7 g as grey solid) in 79% yield.

$(M+H)^+$ 232; $^1$H NMR (400 MHZ, DMSO-$d_6$) δ: 3.97 (s, 3H), 7.14 (d, 1H, J=5.6 Hz), 7.37 (m, 1H), 7.44 (m, 1H), 7.81 (m, 1H), 7.88 (d, 1H, J=5.6 Hz), 12.42, (bs, 1H).

(2B) 2-Dimethylaminomethyl-9-methoxy-4H-thieno[2,3-c]isoquinolin-5-one (7)

9-Methoxy-4H-thieno[2,3-c]isoquinolin-5-one (12.7 g; 54.9 mmol) and N,N-dimethylmethyleneammonium chloride (8.53 g; 91.14 mmol) were placed in a 0.5 L three neck round bottle flask under nitrogen atmosphere. Under stirring, DMF (75 mL) was added followed by acetonitrile (ACN) (190 mL) and the reaction mixture was placed into a preheated oil bath (90° C.). The reaction was complete after 1.5 hrs indicated by a worked up NMR sample.

While still warm, the product was filtered off, washed with ACN, t-butyl methyl ether (TBME) and dried to give 7; 16.8 g, as an off white solid in 94% yield).

$(M+H)^+$ 289; $^1$H NMR (400 MHZ, DMSO-$d_6$) δ: 2.18 (s, 6H); 3.6 (s, 2H); 3.97 (s, 3H), 7.14 (d, 1H, J=5.6 Hz), 7.44 (m, 1H), 7.62 (s, 1H), 7.88 (d, 1H, J=5.6 Hz), 12.42, (bs, 1H).

(2C) 2-Dimethylaminomethyl-9-hydroxy-4H-thieno[2,3-c]isoquinolin-5-one-hydrobromide Under stirring, to a cold (−20° C.) solution of 48% HBr (570 mL) was added 2-dimethylaminomethyl-9-methoxy-4H-thieno[2,3-c]isoquinolin-5-one (16.8 g; 51.7 mmol) all at once. The funnel was rinsed with glacial acetic acid (60 mL) and the resulting dark colored suspension was heated to room temperature over 20 minutes then continued at reflux (135° C. bath temperature) for 24 hrs. At 40° C. the suspension became a black colored solution. The reaction was complete after 24 hrs of refluxing as indicated by worked up TLC, NMR and HPLC samples.

The reaction mixture was cooled to room temperature, and the volatile component was removed under reduced pressure (80° C.) to give a greenish colored solid (22.5 g). This was dissolved in boiling MeOH (210 mL), and treated with charcoal (10 g). The hot solution was filtered off, and the cake was washed with MeOH. The combined MeOH filtrate was concentrated to a volume of 130 mL. Under stirring ether (70 mL) was added over 30 minutes and the product was collected by filtration, washed with methyl-tert-butyl-ether (MTBE), and dried to give 2-dimethylaminomethyl-9-hydroxy-4H-thieno[2,3-c]isoquinolin-5-one-hydro bromine salt (12.7 g; as a greenish solid in 69% yield; mp: 214° C.).

$(M+H)^+$ 275; $^1$H NMR (400 MHZ, DMSO-$d_6$) δ: 2.74 (s, 6H); 4.54 (s, 2H); 7.24 (d, 1H, J=2.3 Hz), 7.33 (m, 1H), 7.74 (d, 1H, J=2.3 Hz), 8.17 (s, 1H), 9.61 (bs, 1H); 10.54 (s, 1H); 12.39, (bs, 1H).

(2D) 2-Dimethylaminomethyl-9-hydroxy-4H-thieno[2,3-c]isoquinolin-5-one-hydrochloride To a solution of 2-dimethylaminomethyl-9-hydroxy-4H-thieno[2,3-c]isoquinolin-5-one-hydrobromide (7 g; 22.5 mmol) under nitrogen atmosphere, in absolute MeOH (300 mL) was gently bubbled HCl (g) over 25 minutes. After 20 minutes some solid started to precipitate. The bubbling of the HCl (g) was stopped and the suspension was stirred at room temperature overnight. Under stirring, ether (300 mL) was added over 20 minutes and the resulting hydrochloride salt was collected by filtration, washed with ether (100 mL), dried at 60° C. in a vacuum oven to give 6.67 g. The ionic chromatography showed 1.13 eq of HCl and the NMR was consistent with the expected product. This and 2.8 g from similar run were combined (9.45 g) and dissolved in hot water (70 mL). Under stirring acetone (800 mL) was added drop wise over 40 minutes, filtered off washed with acetone (100 mL) and dried at 60° C. in a vacuum oven for 24 hours to give 2-dimethylaminomethyl-9-hydroxy-4H-thieno[2,3-c]isoquinolin-5-one-hydro chloride; 7.1 g; 80% yield; HPLC: 99.25%. The ionic chromatography showed 0.93 eq of HCl the content of HCl having dropped to 0.93 eq after recrystallization.

$(M-H)^-$ 273.1; $^1$H NMR (400 MHZ, DMSO-$d_6$) □□ 2.70 (s, 6H); 4.52 (s, 2H); 7.24 (m, 1H); 7.33 (m, 1H), 7.74 (m, 1H), 8.19 (s, 1H); 10.54 (bs, 1H); 10.70 (s, 1H); 12.45, (s, 1H).

Example 3

2-[(Dimethylamino)methyl]thieno[2,3-c]isoquinolin-5(4H)-one hydrochloride

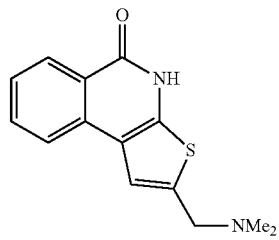 [SMILES: CN(C)Cc1cc2c([nH]c(=O)c3ccccc32)s1]

The title compound was prepared according to the procedure of Example 1, using thieno[2,3-c]isoquinolin-5(4H)-one (Pellicciari, R., Camaioni, E., Costantino, G., Marinozzi, M., Macchiarulo, A., Moroni, F. and Natalini, B., *Farmaco*, 2003, 58, 851-858) in place of 9-methoxythieno[2,3-c]isoquinolin-5(4H)-one.

MS (ES$^+$) m/z 259 (M+H).

Example 4

2-[(Dimethylamino)methyl]-7-fluorothieno-[2,3-c]isoquinolin-5(4H)-one hydrochloride

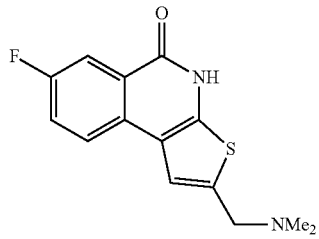 [SMILES: CN(C)Cc1cc2c([nH]c(=O)c3cc(F)ccc32)s1]

Step 1

7-Fluorothieno[2,3-c]isoquinolin-5(4H)-one

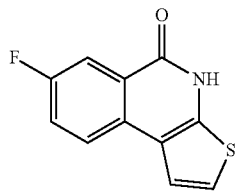 [SMILES: O=c1[nH]c2sccc2c2ccc(F)cc12]

The title compound was prepared according to EXAMPLE 1 of Pellicciari, R., et al., 2006, U.S. Pat. No. 6,989,388, except that 4-bromofluorobenzene was used in place of 2-bromobenzene.

Step 2

2-[(Dimethylamino)methyl]-7-fluorothieno[2,3-c]isoquinolin-5(4H)-one hydrochloride

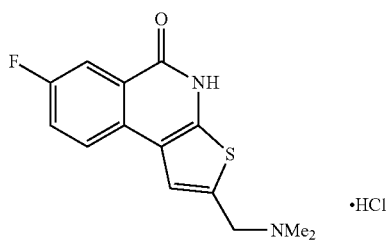 [SMILES: CN(C)Cc1cc2c([nH]c(=O)c3cc(F)ccc32)s1 ; Cl]

The title compound was prepared according to the procedure of Example 1 using the product of Step 1 above as the starting material.

MS (ES$^+$) m/z 277 (M+H).

Example 5

2-[(Dimethylamino)methyl]-9-fluorothieno[2,3-c]isoquinolin-5(4H)-one hydrochloride

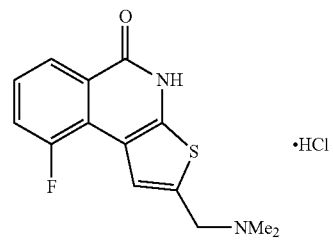 [SMILES: CN(C)Cc1cc2c([nH]c(=O)c3cccc(F)c32)s1 ; Cl]

Step 1

9-Fluorothieno[2,3-c]isoquinolin-5(4H)-one

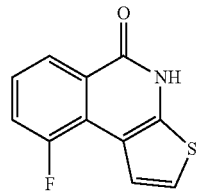 [SMILES: O=c1[nH]c2sccc2c2c(F)cccc12]

The title compound was prepared according to EXAMPLE 1 of Pellicciari, R. and Moroni, F., 2006, U.S. Pat. No. 6,989,388 except that 2-bromofluorobenzene was used in place of 2-bromobenzene.

Step 2

2-[(Dimethylamino)methyl]-9-fluorothieno[2,3-c]isoquinolin-5(4H)-one hydrochloride

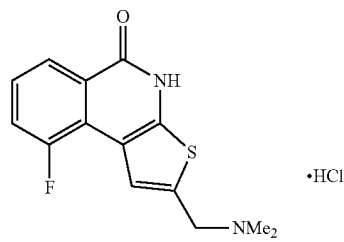 [SMILES: CN(C)Cc1cc2c([nH]c(=O)c3cccc(F)c32)s1 ; Cl]

The title compound was prepared according to the procedure of Example 1 using the product of Step 1 above as the starting material.

MS (ES$^+$) m/z 277 (M+H).

Example 6

8-Chloro-2-[(dimethylamino)methyl]thieno[2,3-c]isoquinolin-5(4H)-one hydrochloride

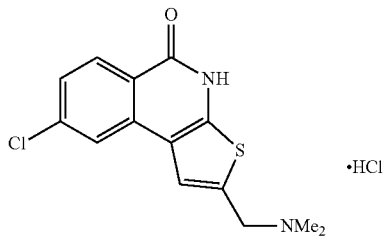 [SMILES: CN(C)Cc1cc2c([nH]c(=O)c3ccc(Cl)cc32)s1 ; Cl]

Step 1

8-Chlorothieno[2,3-c]isoquinolin-5(4H)-one

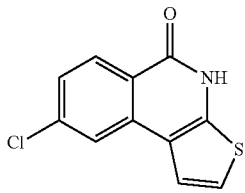 [SMILES: O=c1[nH]c2sccc2c2cc(Cl)ccc12]

The title compound was prepared according to EXAMPLE 1 of Pellicciari, R. and Moroni, F., U.S. Pat. No. 6,989,388, except that 3-bromochlorobenzene was used in place of 2-bromobenzene.

Step 2

8-Chloro-2-[(dimethylamino)methyl]thieno[2,3-c]isoquinolin-5(4H)-one hydrochloride

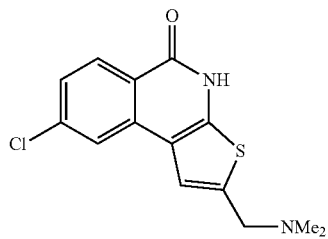

The title compound was prepared according to the procedure of Example 1 using the products of Step 1 above as the starting material.

MS (ES$^+$) m/z 293 (M+H).

Example 7

2-[(Dimethylamino)methyl]-7-fluoro-9-hydroxythieno[2,3-c]isoquinolin-5(4H)-one hydrochloride

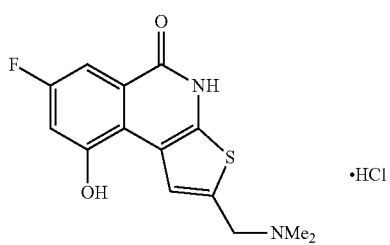 [SMILES: CN(C)Cc1cc2c([nH]c(=O)c3cc(F)cc(O)c32)s1 ; Cl]

Step 1

7-Fluoro-9-methoxythieno[2,3-c]isoquinolin-5(4H)-one

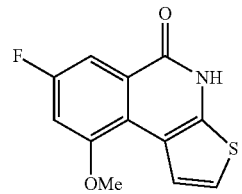 [SMILES: COc1cc(F)cc2c(=O)[nH]c3sccc3c12]

The title compound was prepared according to EXAMPLE 1 of Pellicciari, R. and Moroni, F., 2006, U.S. Pat. No. 6,989,388, except that 2-bromo-5-fluoroanisole was used in place of 2-bromobenzene.

Step 2

2-((Dimethylamino)methyl)-7-fluoro-9-methoxythieno[2,3-c]isoquinolin-5(4H)-one

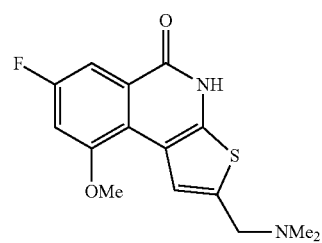 [SMILES: COc1cc(F)cc2c(=O)[nH]c3sc(CN(C)C)cc3c12]

The title compound was prepared according to the procedure of Example 1 using the product of Step 1 above as the starting material.

Step 3

2-((Dimethylamino)methyl)-7-fluoro-9-hydroxythieno[2,3-c]isoquinolin-5(4H)-one hydrochloride

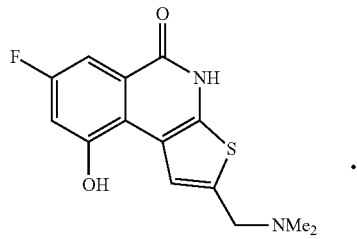

The title compound was prepared according to the procedure of Example 2, using the product of Step 2 above as the starting material.

MS (ES$^+$) m/z 293 (M+H).

Example 8

2-[(Dimethylamino)methyl]-8-methoxythieno[2,3-c]isoquinolin-5(4H)-one hydrochloride

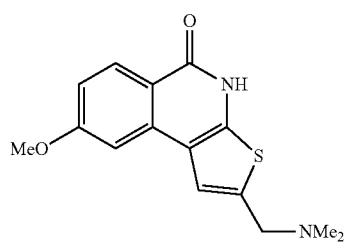

Step 1

8-Methoxythieno[2,3-c]isoquinolin-5(4H)-one

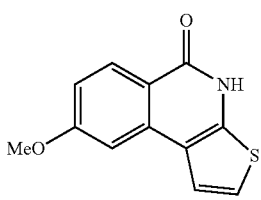 [SMILES: COc1ccc2c(=O)[nH]c3sccc3c2c1]

The title compound was prepared according to EXAMPLE 1 of Pellicciari, R. and Moroni, F., 2006, U.S. Pat. No. 6,989,388, except that 3-bromoanisole was used in place of 2-bromobenzene.

Step 2

2-[(Dimethylamino)methyl]-8-methoxythieno[2,3-c]isoquinolin-5(4H)-one hydrochloride

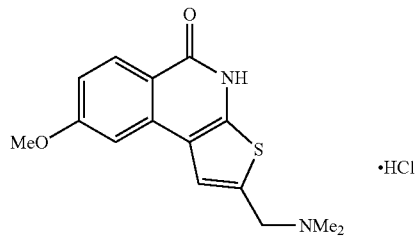 [SMILES: COc1ccc2c(=O)[nH]c3sc(CN(C)C)cc3c2c1 ; Cl]

The title compound was prepared according to the procedure of Example 1 using the product of Step 1 above as the starting material.

MS (ES$^+$) m/z 289 (M+H).

Example 9

2-[(Dimethylamino)methyl]furo[2,3-c]isoquinolin-5(4H)-one hydrochloride

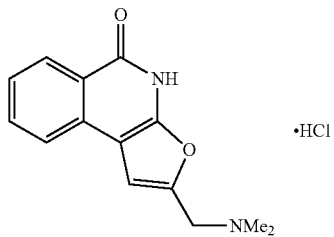 [SMILES: CN(C)Cc1cc2c([nH]c(=O)c3ccccc32)o1 ; Cl]

Step 1

3-Phenyl-2-furancarboxylic acid

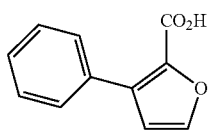 [SMILES: O=C(O)c1occc1-c1ccccc1]

To 3-bromo-2-furancarboxylic acid (540 mg, 2.8 mmol dissolved in DME (105 ml)) was added of (Ph$_3$P)$_4$Pd (936 mg, 0.81 mmol), and the resulting solution was stirred at room temperature for 15 min. The mixture was treated with 500 mg (3.0 mmol) of benzene boronic acid, an aqueous solution of 2M NaHCO$_3$ (4 mmol) and heated to reflux for 10 hours. After cooling to room temperature, the solvent was partially removed under reduced pressure, and the resulting mixture was extracted twice with diethyl ether. The water layer was acidified with 10% HCl and extracted with ethyl acetate (5 times). The combined organic layers were washed with brine, dried (Na$_2$SO$_4$), and evaporated under reduced pressure. The residue was crystallized from a mixture of n-hexane/ethyl acetate (about 8:2) to give the title compound. Yield: 70%.

$^1$H-NMR (CD$_3$OD, 200 MHz) δ 6.57 (d J=1.8 Hz, 1H, H-Fur), 7.16-7.28 (m, 3H, H-Ph), 741-7.49 (m, 2H, H-Ph), 7.59 (d J=1.8 Hz, 1H, H-Fur).

Step 2

Furo[2,3-c]isoquinolin-5(4H)-one

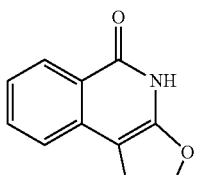

Thionyl chloride (1 ml) was added to a suspension of 3-phenyl-2-furancarboxylic acid (300 mg, 1.46 mmol) in 10 ml of dry benzene and the mixture was refluxed for 2 hours. The solvent and the excess of thionyl chloride were removed under reduced pressure, the residue was taken up using 10 ml of dry THF and cooled to 0° C. Sodium azide (1.5 mmol) dissolved in the minimal amount of water was quickly added and the resulting solution was stirred for 1 hour at room temperature. After pouring into 100 ml of cracked ice/H$_2$O and extraction with diethyl ether (4×100 ml), and the collected organic layers were dried over Na$_2$SO$_4$. The filtrate was gently evaporated under reduced pressure, the residue was dissolved in 10 ml of o-dichlorobenzene, and the resulting mixture was refluxed for 5-10 hours. The mixture was then cooled, and directly submitted to the flash chromatography, elution with dichloromethane/methanol (99/1) afforded to the title compound. Yield: 68%.

mp 216-218° C.

$^1$H-NMR (DMSO, 400 MHz) δ 7.28 (d J=2.0 Hz, 1H, H-Fur), 7.46 (t J=7.8 Hz, 1H, H-Ph), 7.69 (d J=2.0 Hz, 1H, H-Fur), 7.77 (t J=7.9 Hz, 1H, H-Ph), 7.99 (d J=7.9 Hz, 1H, H-Ph), 8.24 (d J=8.0 Hz, 1H, H-Ph), 13.1 (s, 1H, NH).

Step 3

2-[(Dimethylamino)methyl]furo[2,3-c]isoquinolin-5(4H)-one hydrochloride

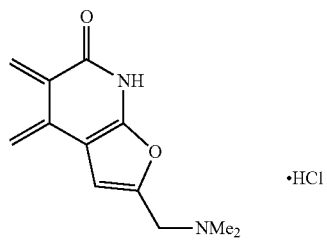 [SMILES: C=c1c(=O)[nH]c2oc(CN(C)C)cc2c1=C ; Cl]

Furo[2,3-c]isoquinolin-5(4H)-one (55 mg, 0.27 mmol) was dissolved in a mixture of dry dimethylformamide (1 ml) and dry acetonitrile (2 ml) and treated with N,N-dimethyl (methylene)ammonium chloride (1 mmol) prepared according to known procedure (Kinast G. et al. *Angew. Chem. Int. Ed. Engl.* 1976, 15(4), 239-240; Bohme H. et al. *Chem. Ber.* 1960, 93, 1305). The reaction mixture was refluxed overnight, and the resulting precipitate was filtered and washed with dry diethyl ether to give the title compound. Yield: 65%.

mp>200° C.

$^1$H-NMR (CD$_3$OD, 400 MHz) δ 2.97 (s, 6H, N(CH$_3$)$_2$), 4.57 (s, 2H, NCH$_2$), 7.46 (s, 1H, H-Fur), 7.51 (t J=7.8 Hz, 1H, H-Ph), 7.80 (t J=7.9 Hz, 1H, H-Ph), 7.93 (d J=7.9 Hz, 1H, H-Ph), 8.34 (d J=8.0 Hz, 1H, H-Ph).

$^{13}$C-NMR (CD$_3$OD, 100.6 MHz) δ 41.3, 52.7, 101.5, 110.9, 122.3, 125.3, 127.8, 132.7, 132.9, 139.4, 150.2, 158.5, 162.1.

Example 10

9-Hydroxy-2-(morpholin-4-ylmethyl)thieno[2,3-c]isoquinolin-5(4H)-one

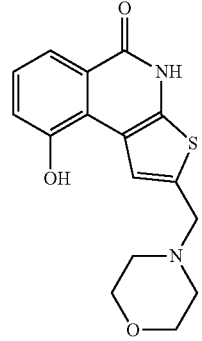 [SMILES: O=c1[nH]c2sc(CN3CCOCC3)cc2c2c(O)cccc12]

Step 1

9-Methoxy-2-(morpholinomethyl)thieno[2,3-c]isoquinolin-5(4H)-one

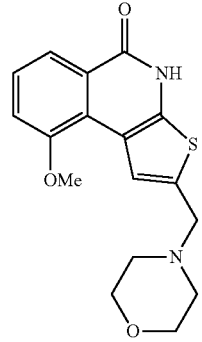 [SMILES: COc1cccc2c(=O)[nH]c3sc(CN4CCOCC4)cc3c12]

Morpholine (950 µL, 0.011 mmol) was added slowly to a solution of 9-hydroxythieno[2,3-c]isoquinolin-5(4H)-one in 2.6 mL of 37% aqueous formaldehyde and the resulting reaction mixture was refluxed for 7 hours. The reaction was monitored by TLC until all starting material is consumed. After cooling to room temperature, the reaction mixture was partitioned between water and ethyl acetate, the organics were separated, washed with brine, dried over Na$_2$SO$_4$ and solvent was evaporated under reduced pressure to produce the title compound as a pale solid.

MS (ES$^+$) m/z 331 (M+H).

Step 2

9-Hydroxy-2-(morpholin-4-ylmethyl)thieno[2,3-c]isoquinolin-5(4H)-one

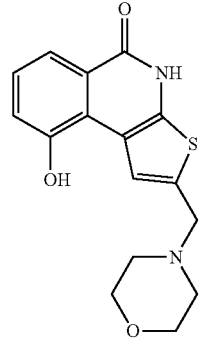 [SMILES: O=c1[nH]c2sc(CN3CCOCC3)cc2c2c(O)cccc12]

The title compound was prepared according to the procedure of Example 2 using the product of Step 1 above as the starting material.
MS (ES⁺) m/z 317 (M+H).

Example 11

9-Hydroxy-2-(piperidin-1-ylmethyl)thieno[2,3-c]isoquinolin-5(4H)-one

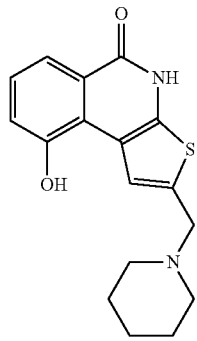 [SMILES: O=c1[nH]c2sc(CN3CCCCC3)cc2c2c(O)cccc12]

Step 1

9-Methoxy-2-(piperidin-1-ylmethyl)thieno[2,3-c]isoquinolin-5(4H)-one

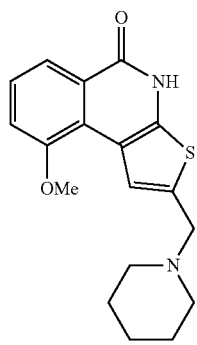 [SMILES: COc1cccc2c(=O)[nH]c3sc(CN4CCCCC4)cc3c12]

The title compound was prepared according to the procedure of Example 10, Step 1 above except that piperidine was used in place of morpholine.
MS (ES⁺) m/z 329 (M+H).

Step 2

9-Hydroxy-2-(piperidin-1-ylmethyl)thieno[2,3-c]isoquinolin-5(4H)-one

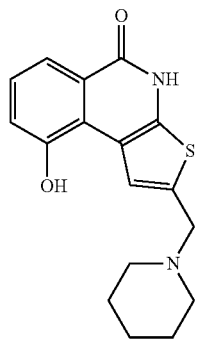 [SMILES: O=c1[nH]c2sc(CN3CCCCC3)cc2c2c(O)cccc12]

The title compound was prepared according to the procedure of Example 2.
MS (ES⁺) m/z 315 (M+H).

Example 12

9-Hydroxy-2-(1,3-thiazolidin-3-ylmethyl)thieno[2,3-c]isoquinolin-5(4H)-one

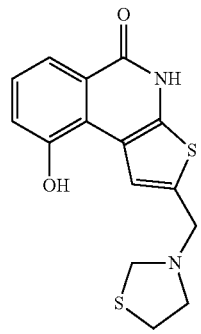 [SMILES: O=c1[nH]c2sc(CN3CCSC3)cc2c2c(O)cccc12]

Step 1

9-Methoxy-2-(thiazolidin-3-ylmethyl)thieno[2,3-c]isoquinolin-5(4H)-one

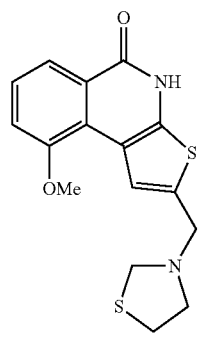 [SMILES: COc1cccc2c(=O)[nH]c3sc(CN4CCSC4)cc3c12]

The title compound was prepared according to the procedure of Example 10, Step 1 above except that thiazolidine was used in place of morpholine.
MS (ES⁺) m/z 333 (M+H).

Step 2

9-Hydroxy-2-(1,3-thiazolidin-3-ylmethyl)thieno[2,3-c]isoquinolin-5(4H)-one

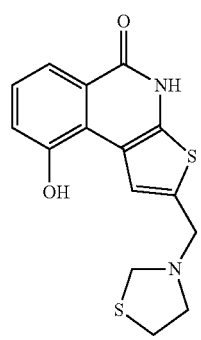 [SMILES: O=c1[nH]c2sc(CN3CCSC3)cc2c2c(O)cccc12]

The title compound was prepared according to the procedure of Example 2.
MS (ES⁺) m/z 319 (M+H).

Example 13

9-Hydroxy-2-{[(1-methylethyl)amino]methyl}thieno[2,3-c]isoquinolin-5(4H)-one

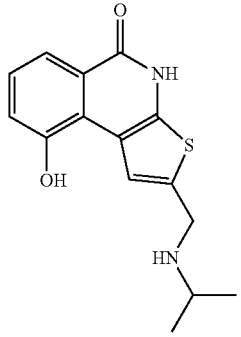 [SMILES: CC(C)NCc1cc2c([nH]c(=O)c3cccc(O)c32)s1]

Step 1

2-((Isopropylamino)methyl)-9-methoxythieno[2,3-c]isoquinolin-5(4H)-one

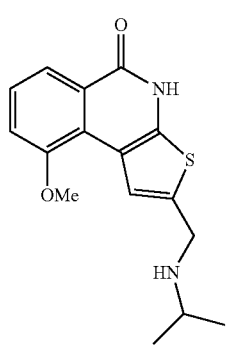 [SMILES: COc1cccc2c(=O)[nH]c3sc(CNC(C)C)cc3c12]

The title compound was prepared according to the procedure of Example 10, Step 1 above except that isopropylamine was used in place of morpholine.
MS (ES$^+$) m/z 303 (M+H).

Step 2

9-Hydroxy-2-{[(1-methylethyl)amino]methyl}thieno[2,3-c]isoquinolin-5(4H)-one

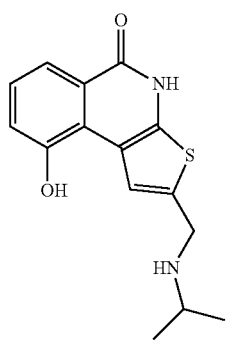 [SMILES: CC(C)NCc1cc2c([nH]c(=O)c3cccc(O)c32)s1]

The title compound was prepared according to the procedure of Example 2.
MS (ES$^+$) m/z 289 (M+H).

Example 14

9-Hydroxy-2-(pyrrolidin-1-ylmethyl)thieno[2,3-c]isoquinolin-5(4H)-one

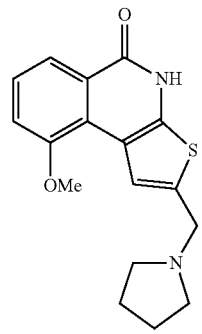 [SMILES: COc1cccc2c(=O)[nH]c3sc(CN4CCCC4)cc3c12]

Step 1

9-Methoxy-2-(pyrrolidin-1-ylmethyl)thieno[2,3-c]isoquinolin-5(4H)-one

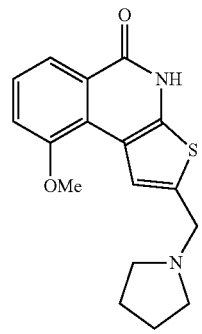

The title compound was prepared according to the procedure of Example 10, Step 1 above except that pyrrolidine was used in place of morpholine.
MS (ES$^+$) m/z 315 (M+H).

Step 2

9-Hydroxy-2-(pyrrolidin-1-ylmethyl)thieno[2,3-c]isoquinolin-5(4H)-one

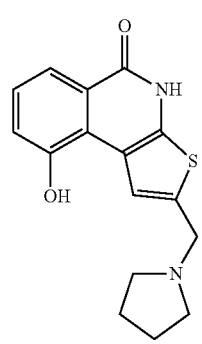

The title compound was prepared according to the procedure of Example 2.
MS (ES$^+$) m/z 301 (M+H).

Example 15

2-[(4-Bromopiperidin-1-yl)methyl]-9-hydroxythieno[2,3-c]isoquinolin-5(4H)-one

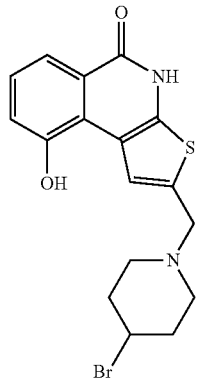 [SMILES: O=c1[nH]c2sc(CN3CCC(Br)CC3)cc2c2c(O)cccc12]

Step 1

2-((4-Bromopiperidin-1-yl)methyl)-9-methoxythieno[2,3-c]isoquinolin-5(4H)-one

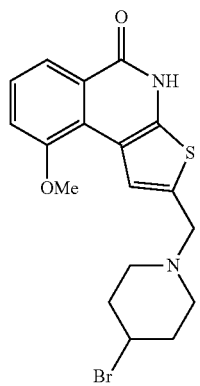 [SMILES: COc1cccc2c(=O)[nH]c3sc(CN4CCC(Br)CC4)cc3c12]

The title compound was prepared according to the procedure of Example 10, Step 1 above except that 4-bromopiperidine was used in place of morpholine.

MS (ES+) m/z 408 (M+H).

Step 2

2-[(4-Bromopiperidin-1-yl)methyl]-9-hydroxythieno[2,3-c]isoquinolin-5(4H)-one

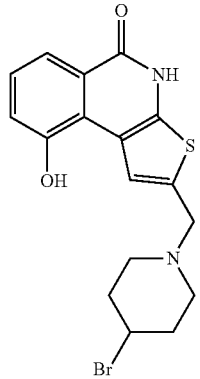 [SMILES: O=c1[nH]c2sc(CN3CCC(Br)CC3)cc2c2c(O)cccc12]

The title compound was prepared according to the procedure of Example 2

MS (ES+) m/z 394 (M+H).

Example 16

2-[(Dibenzylamino)methyl]-9-hydroxythieno[2,3-c]isoquinolin-5(4H)-one

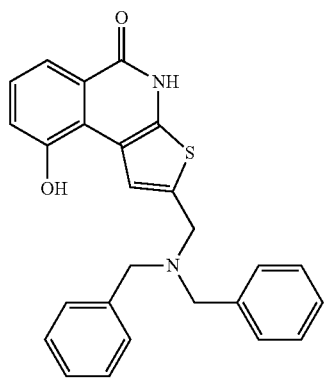 [SMILES: O=c1[nH]c2sc(CN(Cc3ccccc3)Cc3ccccc3)cc2c2c(O)cccc12]

Step 1

2-((Dibenzylamino)methyl)-9-methoxythieno[2,3-c]isoquinolin-5(4H)-one

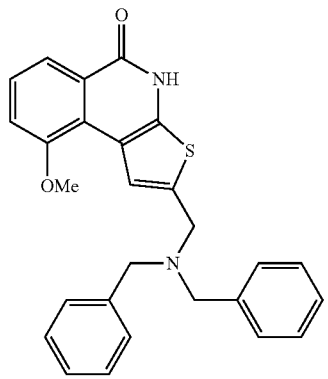 [SMILES: COc1cccc2c(=O)[nH]c3sc(CN(Cc4ccccc4)Cc4ccccc4)cc3c12]

The title compound was prepared according to the procedure of Example 10, Step 1 above except that dibenzylamine was used in place of morpholine.

MS (ES+) m/z 441 (M+H).

Step 2

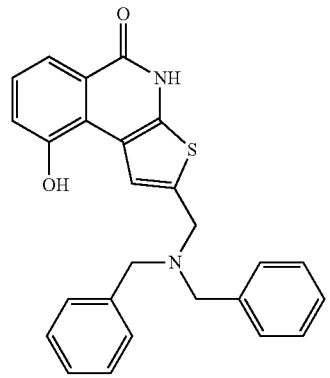 [SMILES: O=c1[nH]c2sc(CN(Cc3ccccc3)Cc3ccccc3)cc2c2c(O)cccc12]

The title compound was prepared according to the procedure of Example 2.
MS (ES⁺) m/z 427 (M+H).

Example 17

2-{[Benzyl(methyl)amino]methyl}-9-hydroxythieno[2,3-c]isoquinolin-5(4H)-one

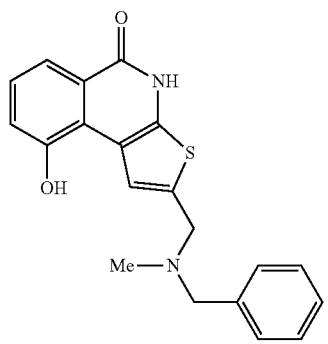 [SMILES: CN(Cc1ccccc1)Cc1cc2c([nH]c(=O)c3cccc(O)c32)s1]

Step 1

2-((Benzyl(methyl)amino)methyl)-9-methoxythieno[2,3-c]isoquinolin-5(4H)-one

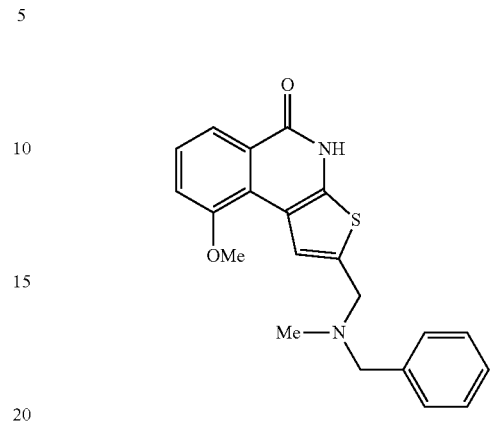

The title compound was prepared according to Example 10, Step 1 above except that N-methyl-N-benzylamine was used in place of morpholine.
MS (ES⁺) m/z 365 (M+H).

Step 2

2-{[Benzyl(methyl)amino]methyl}-9-hydroxythieno[2,3-c]isoquinolin-5(4H)-one

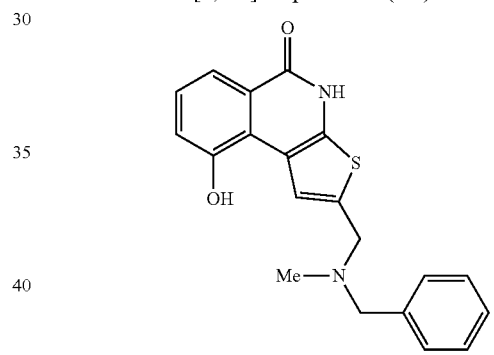

The title compound was prepared according to the procedure of Example 2.
MS (ES⁺) m/z 351 (M+H).

Example 18

Functional Assessment of Human PARP-1 Enzymatic Activity

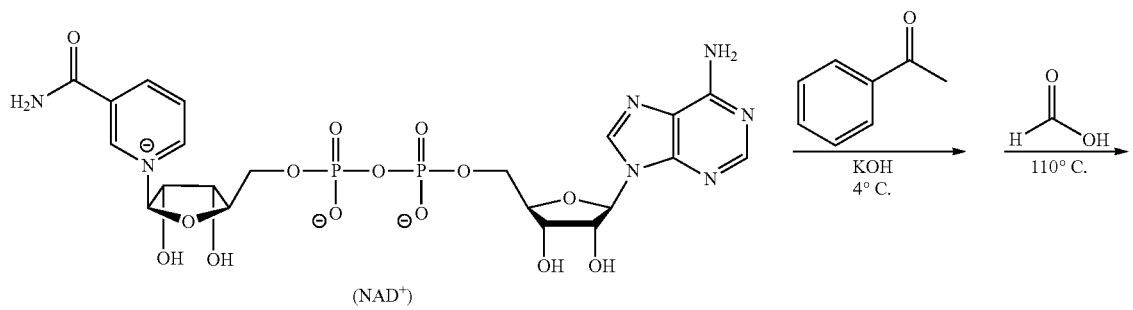

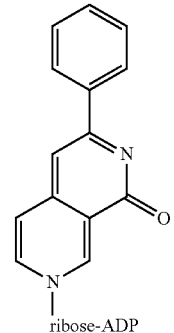

1
fluorescece excitation at 372 nm,
emmision at 444 nm

Materials and Reagents:

hrPARP-1 (human recombinant, Trevigen), Activated DNA (Sigma), 6(5H)-phenanthridinone (PND), (Sigma), NAD+ (Calbiochem), PARP-1 assay buffer (50 mM Tris, 2 mM $MgCl_2$, pH 8.0), 20% acetophenone in EtOH, 2 M KOH 88% formic acid, 110° C. oven, Flexstation Plate Reader.

Procedure:

Compound plates were prepared by making a series of 1:3 dilutions for each tested compound, 10 steps of each at 20 μL in DMSO starting from a concentration of 5 mM. $NAD^+$ (39 μL of a 6.4 μM solution) were added to each well of a 96-well flat bottom fluorescent assay plate. Test compound (1 μL) was added to each well. To initiate the reaction, 10 μL of PARP (contains 5 U of PARP and 75 μg/mL activated DNA) was added with a final 1 U hrPARP-1, 15 μg/mL activated DNA and 5 μM of $NAD^+$. The highest concentration used for test compounds was 100 μM. The plates were incubated at room temperature on a shaker. After 20 min, 20 μL of 2 M KOH and 20 μL of 20% acetophenone were added. The plate was incubated 10 min. at 4° C., and 90 μL of 88% formic acid was added. After incubating in an 110° C. oven for 5 min, the plate was cooled to room temperature and read of a Flexstation Plate Reader (excitation at 360 nm, emission at 445 nm).

Analysis of Results:

LSW data analysis software was used to generate PARP-1 $IC_{50}$s. The results are presented in Table 1.

Example 19

In Vitro Brain Exposure Studies

1. MDCK Permeability Assay

Multi Drug Resistance-Madin-Darby Canine Kidney (MDR-MDCK) cells were obtained from NIH (Bethesda, Md., USA). Cells were plated on Costar 3401 Transwell 12 well, 12 mm diameter, 0.4 um pore size plates (Costar, Mass., USA) and cultured for at least 6 days prior to the transport assay. The cells were carefully pre-washed with Hank's balanced salt solution containing 10 mM HEPES and 15 mM D-glucose at pH 7.4, which was also used as the assay buffer. The test compounds were dosed on the apical side (A-B) or the basolateral side (B-A) with 0.2 mM Lucifer Yellow (500 μL into apical side, 1500 μL into basolateral side). The test compounds in the apical or basolateral chambers were at an initial concentration of 10 μM. The plates were incubated at 37° C. with 5% $CO_2$ and 90% relative humidity for 2 hours. One hundred microliters of receiver solution (basolateral side for A-B transport experiment, apical side for B-A transport experiment) was transferred to a 96 well plate for LC-MS-MS quantization of the test compound concentration and fluorometer quantization of Lucifer Yellow. The results are presented in Table 1.

Quality control compounds and TEER measurements were run to assure proper operation of the assay (see Table 2). The TEER values of each well use for the assay should be ≥1400 ohm·$cm^2$.

TABLE 1

| EXAMPLE # | $IC_{50}$ (nM) | MDCK Efflux Ratio |
|---|---|---|
| 1 | 137 | |
| 2 | 28 | 1.7 |
| 3 | 260 | |
| 4 | 100 | |
| 5 | 200 | |
| 6 | 2250 | |
| 7 | 38 | |
| 8 | 2187 | |
| 9 | 161 | |
| 10 | 5.6 | 3.1 |
| 11 | 4.7 | 10.4 |
| 12 | 3.3 | 0.8 |
| 13 | 86 nM | not done |
| 14 | 81 nM | >20 |
| 15 | 35 nM | 0.9 |
| 16 | 1057 nM | |
| 17 | 373 nM | |

TABLE 2

| QC Acceptance Criteria | |
|---|---|
| Compound | Acceptable Range of Papp Values ($10^{-6}$ cm/s) |
| Atenolol | <0.50 |
| Propranolol | 10-30 |
| Digoxin | Efflux Ratio Papp(B-A)/Papp (A-B) > 10 |
| Lucifer Yellow | <0.40 |

2. Brain (B)-Plasma (P) Dialysis

Dialysis membrane strips with MWCO 3.5 KD were immersed gently into HPLC water for 20 min, then into 30% ethanol/water for 15 min, rinsed with water, and soaked in PBS for 20 min before use. DMSO stock solution of 1 mM was prepared and 10 μL was added to 990 uL plasma (1 plasma:3 PBS) or brain homogeneous (1 brain:12 PBS). The final concentration was 10 μM test compound with 1%

DMSO. The dialysis was setup with 200 uL PBS vs. 200 uL diluted plasma or diluted brain homogenates with test compounds. The dialysis plate was incubated at 37° C., 70 RPM for 5 hours. At the end of the incubation, 150 μL PBS, 50 uL plasma and 50 uL of brain homogenates were sampled from the dialysis device. Each of the samples was matched with PBS, plasma and brain homogenates to give consistent matrix material. Cold acetonitrile of 300 μL was added to the sample to precipitate the proteins and tissues. The solutions were centrifuged and the supernatants were transferred for LC-MS-MS analysis. Four replicates were preformed for each test compound. Data was calculated according to Summerfield S G, Read K, Begley D J, Obradovic T, Hidalgo I J, Coggon S, Lewis A V, Porter R A, Jeffrey P 2007. Central Nervous System Drug Disposition: The Relationship between in Situ Brain Permeability and Brain Free Fraction. J Pharmacol Exp Ther 322(1):205-213 and is provided in Table 3.

Example 20

Analysis of Microsomal Stability

The assay protocol was described in Summerfield S G, Read K, Begley D J, Obradovic T, Hidalgo I J, Coggon S, Lewis A V, Porter R A, Jeffrey P 2007. Central Nervous System Drug Disposition: The Relationship between in Situ Brain Permeability and Brain Free Fraction. J Pharmacol Exp Ther, 322(1):205-213; and Li Di, E. Kerns, S. Li, S. Petusky, "High Throughput Metabolic Stability Assay for Insoluble Compounds", Int. J. Pharm., 317, 54-60, 2006.

The samples were incubated with liver microsomes from rat, mouse, and human at 1 μM at microsomal protein concentration of 0.5 mg/mL at 37° C. in the presence of NADPH cofactor. At both time 0 and 15 minutes incubation, cold acetonitrile was added to the wells to stop the reaction. The solution was centrifuged and the supernatants were analyzed using LC-MS-MS. "Phase I" represents Phase I metabolism-oxidative metabolism by microsomes and "Phase II" represents Phase I oxidative metabolism (stated above) plus cofactors added that allow for Phase II (non-oxidative, conjugative) metabolism to take place.

The results are presented in Table 3.

3. Charged 32.2 μL of 0.1 N NaOH (1 eq). Free base precipitated.
4. Filtered
5. Dried at 40° C. in vacuum oven under $N_2$ purge.

Monohydrate Procedure:
1. Charged 1 g of 2-Dimethylaminomethyl-9-hydroxythieno[2,3-c]isoquinolin-5(4H)-one hydrobromide salt.
2. Charged 26 mL of water. Stir until fully dissolved.
3. Charge 28.1 μL of 0.1 N NaOH (1 eq). Free base precipitated.
4. Filtered
5. Dried at 40° C. in vacuum oven under $N_2$ purge.

Experimental

Analytical Data

Different crystalline forms of a particular form may be distinguished from each other by different XRPD patterns, thereby signifying different crystal lattices. An XRPD pattern of reflection (peaks) is typically considered a fingerprint of a particular crystalline form. It is well known that relative intensities of the XRPD peaks can vary depending upon, inter alia, sample preparation technique, crystal size distribution, various filters used, the sample mounting technique, and the particular instrument employed. In some instances, new peaks may be observed or existing peaks may disappear, depending upon the type of instrument or the settings. As used herein, "peak" or "characteristic peak" refers to a reflection having a relative height/intensity of at least about 3% of the maximum peak height/intensity. Moreover, instrument variations and other factors can affect the 2-theta values. Thus peak assignments, such as those reported here, can vary by plus or minus about 0.2° (2-theta), and the term substantially as used in the context of XRPD herein is meant to encompass the above-mentioned variations. In the same way, temperature readings in connection with DSC, TGA or other thermal experiments can vary about +/−3° C. depending upon the instrument, particular settings, sample preparation etc.

TABLE 3

| | Microsomal Stability Rat | | Microsomal Stability C57 Mouse | | Microsomal Stability Human | | Brain-Plasma Dialysis | |
|---|---|---|---|---|---|---|---|---|
| Ex. # | Phase I $t_{1/2}$ (min) | Phase I & II $t_{1/2}$ (min) | Phase I $t_{1/2}$ (min) | Phase I & II $t_{1/2}$ (min) | Phase I $t_{1/2}$ (min) | Phase I & II $t_{1/2}$ (min) | B/P Ratio | B/P/efflux ratio (ER) |
| 11 | 10 | 18 | 27 | >30 | 19 | 17 | 1.25 | 0.12 |
| 10 | 30 | >30 | >30 | >30 | >30 | 30 | 0.81 | 0.04 |
| 12 | 5 | 5 | 4 | 5 | 6 | 4 | 0.79 | 0.79 |
| 13 | <1 | <1 | 28 | 24 | >30 | >30 | 1.53 | not done |
| 14 | >30 | >30 | >30 | >30 | >30 | >30 | 1.03 | <0.05 |
| 15 | 3 | 3 | 4 | 3 | 7 | 5 | 1.12 | 1.12 |
| 2 | 6 | <1 | 15 | 19 | >30 | 17 | 0.05 | 0.03 |

Example 21

Preparation and Analysis of Anhydrous and Monohydrate Free Base Forms of 2-Dimethylaminomethyl-9-hydroxythieno[2,3-c]isoquinolin-5(4H)-one Anhydrous Procedure:
1. Charged 1 g of 2-Dimethylaminomethyl-9-hydroxythieno[2,3-c]isoquinolin-5(4H)-one hydrochloride salt.
2. Charged 10 mL of water. Stirred until fully dissolved.

Accordingly, a crystalline form reported herein having a DSC thermograph "substantially" as shown is understood to accommodate such variation.

X-ray diffraction data was acquired using a Rigaku Miniflex X-ray powder diffractometer using the following parameters: Cu K alpha source run at 400 W, voltage 30 kV, current 15.0 mA, scan range (2θ) 3 to 40° at 2°/min, scan step size 0.02°. The crystalline monohydrate form of 2-dimethylaminomethyl-9-hydroxythieno[2,3-c]isoquinolin-5(4H)-one is characterized according to the XRPD pattern substantially as shown in FIG. 1 (See Table 4 for peak data).

TABLE 4

| Pos. [°2Th.] | d-spacing [Å] | Rel. Int. [%] |
|---|---|---|
| 8.2900 | 10.66592 | +++ |
| 8.6154 | 10.26370 | +++ |
| 10.3478 | 8.54895 | ++ |
| 11.7236 | 7.54863 | +++ |
| 15.3362 | 5.77764 | +++ |
| 16.4034 | 5.40407 | +++ |
| 16.5751 | 5.34847 | +++ |
| 18.3869 | 4.82535 | ++ |
| 18.9452 | 4.68439 | +++ |
| 19.4049 | 4.57445 | +++ |
| 21.2948 | 4.17254 | ++ |
| 21.8292 | 4.07159 | +++ |
| 22.3280 | 3.98174 | ++ |
| 22.6210 | 3.93083 | ++ |
| 23.1346 | 3.84471 | ++ |
| 23.2598 | 3.82429 | ++ |
| 23.4887 | 3.78755 | ++ |
| 23.7071 | 3.75315 | +++ |
| 24.9013 | 3.57579 | ++ |
| 25.3997 | 3.50676 | +++ |
| 25.6625 | 3.47143 | +++ |
| 26.3133 | 3.38704 | ++ |
| 28.0053 | 3.18613 | + |
| 28.7425 | 3.10606 | +++ |
| 29.8782 | 2.99054 | + |
| 31.0513 | 2.88018 | ++ |
| 32.6655 | 2.74145 | ++ |
| 33.8221 | 2.65030 | ++ |
| 34.2165 | 2.62065 | ++ |
| 34.6840 | 2.58639 | + |
| 35.4706 | 2.53082 | ++ |
| 36.3247 | 2.47324 | ++ |
| 37.7532 | 2.38289 | + |
| 38.8400 | 2.31867 | ++ |
| 39.5722 | 2.27745 | + |

In some aspects of the invention the crystalline anhydrous form of 2-dimethylaminomethyl-9-hydroxythieno[2,3-c]isoquinolin-5(4H)-one thereof have at least 3 characteristic 2θ values measured using CuKα radiation selected from 8.3, 8.6, 11.7, 18.4, 18.9, 19.4, 25.7 and 28.7.

The crystalline anhydrous form of 2-dimethylaminomethyl-9-hydroxythieno[2,3-c]isoquinolin-5(4H)-one is characterized according to the XRPD pattern substantially as shown in FIG. 1 (See Table 5 for peak data).

TABLE 5

| Pos. [°2Th.] | d-spacing [Å] | Rel. Int. [%] |
|---|---|---|
| 10.3585 | 8.54013 | +++ |
| 10.6401 | 8.31473 | ++ |
| 14.5067 | 6.10610 | ++ |
| 16.6484 | 5.32511 | ++ |
| 21.2940 | 4.17270 | +++ |
| 22.5123 | 3.94957 | ++ |
| 22.8847 | 3.88613 | +++ |
| 24.8608 | 3.58153 | ++ |
| 25.5530 | 3.48607 | + |
| 26.1590 | 3.40666 | + |
| 26.8180 | 3.32443 | +++ |
| 27.2322 | 3.27480 | + |
| 28.0515 | 3.18098 | + |
| 31.7346 | 2.81970 | + |
| 32.1400 | 2.78506 | ++ |
| 35.4067 | 2.53524 | ++ |

TABLE 5-continued

| Pos. [°2Th.] | d-spacing [Å] | Rel. Int. [%] |
|---|---|---|
| 38.5458 | 2.33569 | + |
| 38.7887 | 2.32162 | + |

In some aspects of the invention the crystalline anhydrous form of 2-dimethylaminomethyl-9-hydroxythieno[2,3-c]isoquinolin-5(4H)-one thereof have at least 3 characteristic 2θ values measured using CuKα radiation selected from 10.4, 10.6, 14.5, 21.3, 26.8 and 32.1.

In each table, intensities are provided as relative intensities such that +++ represents an intensity that is equal to or greater than 20% of the maximum intensity, ++ represents an intensity that is equal to or greater than 5% of the maximum intensity but less than 20% of the maximum intensity, and the + represents an intensity that is less than 5% of the maximum intensity (but greater than 3%).

Figure 2:
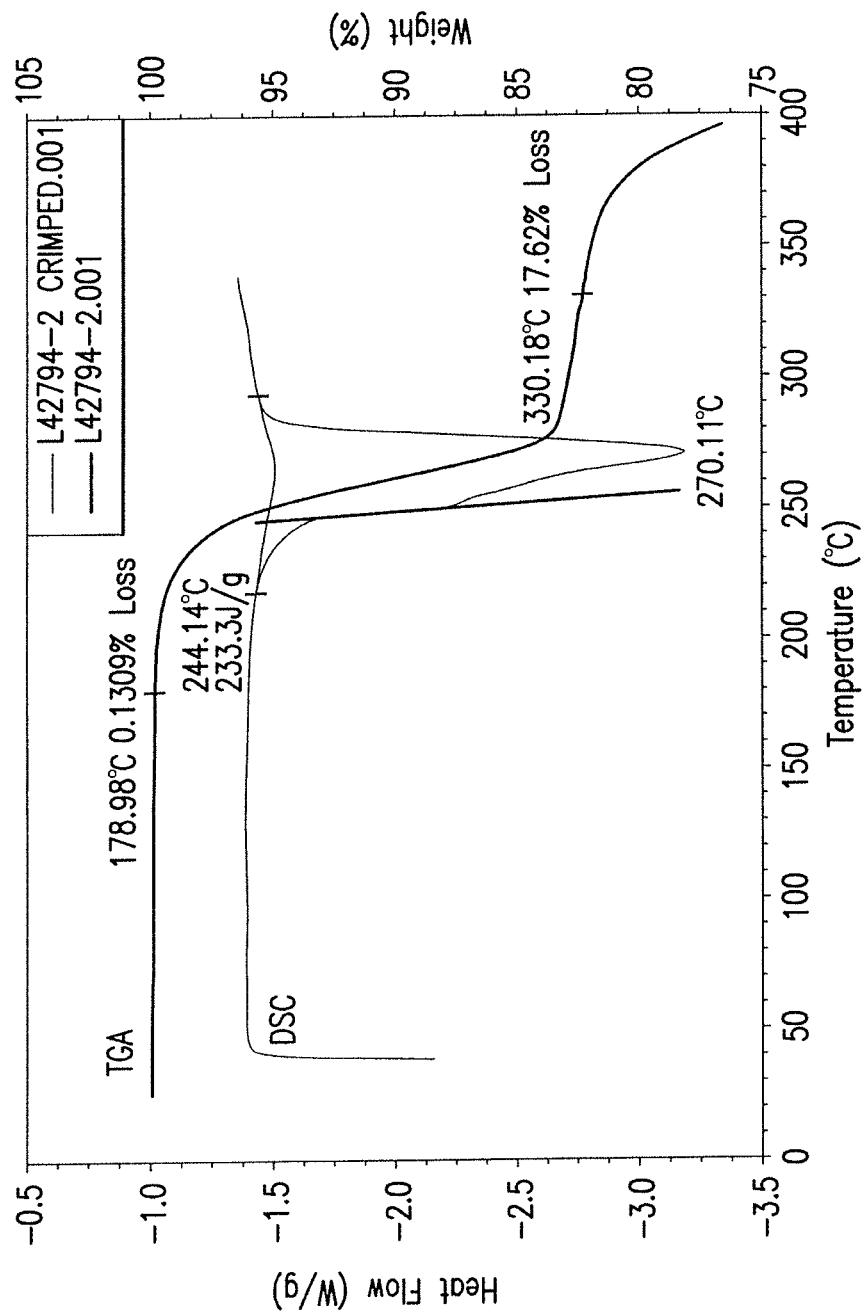
FIG. 2 shows TGA and DSC scans for the anhydrous form of 2-dimethylaminomethyl-9-hydroxythieno[2,3-c]isoquinolin-5(4H)-one.
Figure 3:
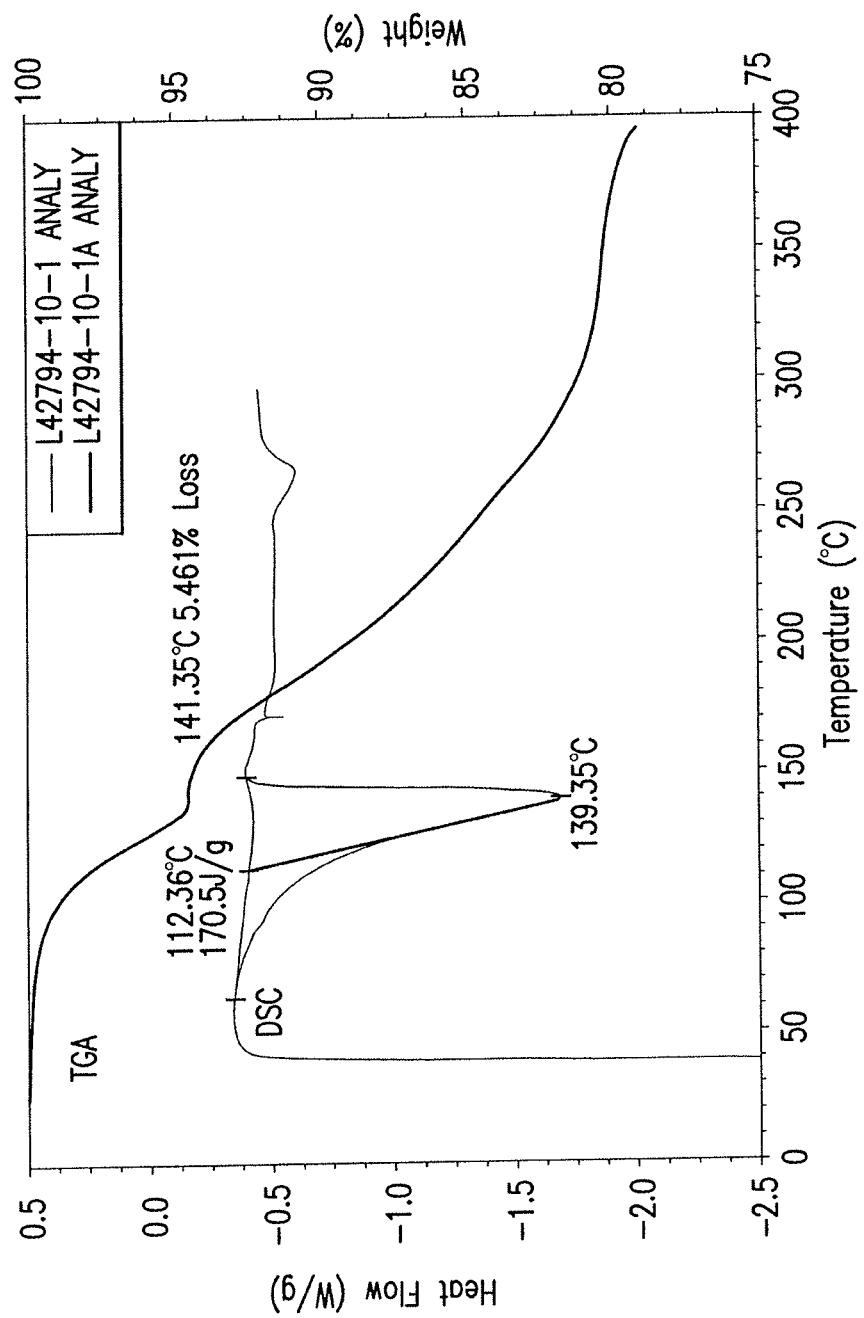
FIG. 3 shows TGA and DSC scans for the monohydrate form of 2-dimethylaminomethyl-9-hydroxythieno[2,3-c]isoquinolin-5(4H)-one.

Differential scanning calorimetry (DSC) data was collected using a TA instruments model Q1000 using the following parameters: 50 mL/min. purge gas ($N_2$); scan range 40 to 275° C. at 10° C./min. shown in FIG. 2 for the anhydrous form and FIG. 3 for the monohydrate form. Thermogravimetric analysis (TGA) was collected using a TA instruments model Q500 using the following parameters: 50 mL/min. purge gas ($N_2$); scan range up to 400° C. at 10° C./min. shown in FIG. 2 for the anhydrous form and FIG. 3 for the monohydrate form. The hydrate that was obtained contained 6.54 wt. % water (theoretical 1 mole of water=6.16 wt. %). When heated past the endotherm, the monohydrate converts to amorphous form. This amorphous material does not show evidence of recrystallization upon heating in DSC.

Both the monohydrate form and the anhydrous form can be produced by seeding. The HBr salt can be dissolved in 5 volumes of water by heating to 90° C. After the solution is seeded (with either the monohydrate form or the anhydrous form), 1 equivalent of 1N NaOH can be added to crystallize material and it can then be filtered and dried. The anhydrous form can be converted to the monohydrate form by exposure to humidity.

Figure 4:
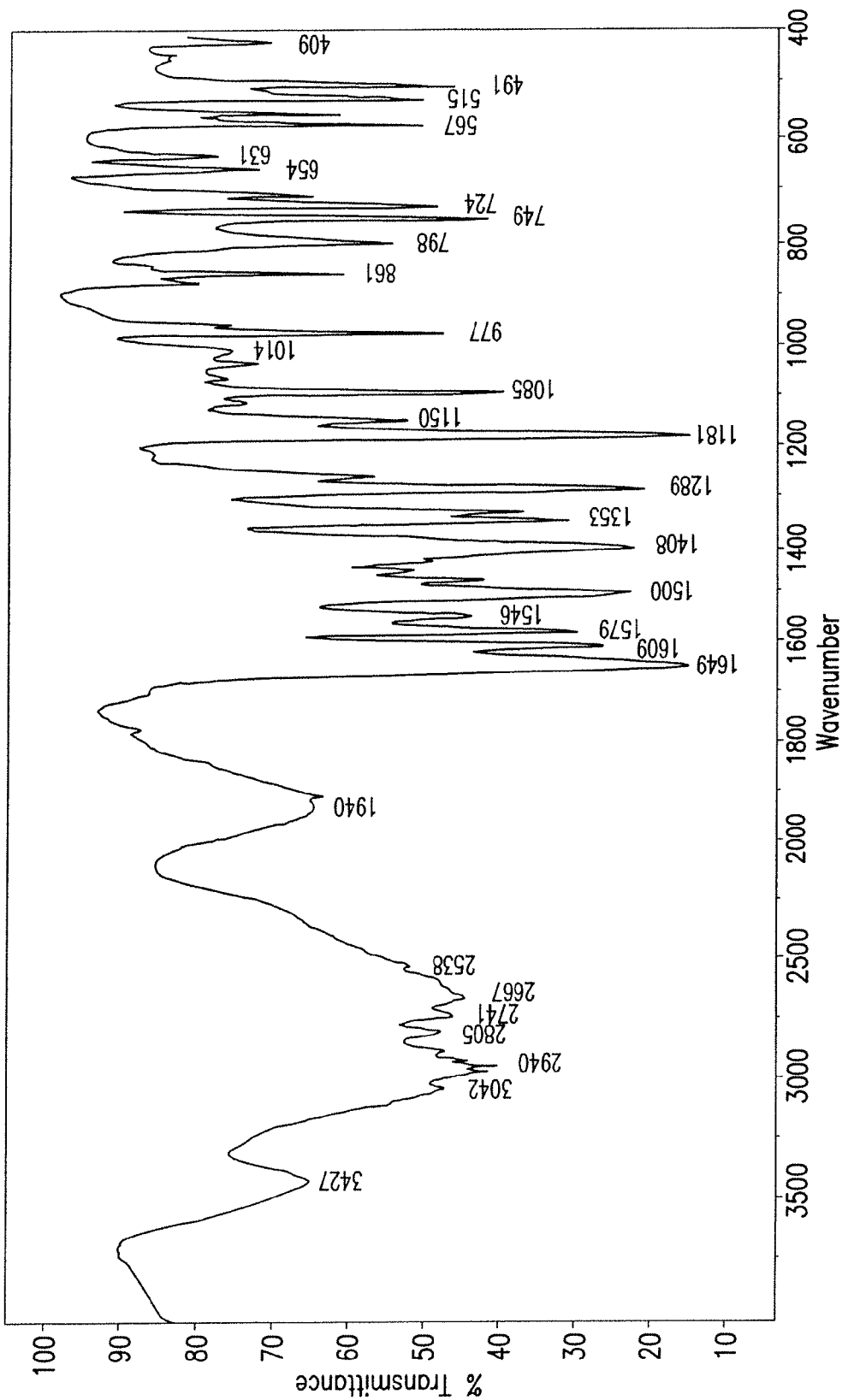
FIG. 4 shows an infrared (IR) spectrum for the anhydrous free base form of 2-dimethylaminomethyl-9-hydroxythieno[2,3-c]isoquinolin-5(4H)-one.

FIG. 4 shows an infrared (IR) spectrum for the anhydrous free base form of 2-dimethylaminomethyl-9-hydroxythieno[2,3-c]isoquinolin-5(4H)-one with absorbances at 2150-2800 cm-1 (broad) and 1940 cm-1 which are indicative of a protonated amine species in the solid state. The IR spectral analysis was performed by the KBr disc sample preparation wherein the sample was finely ground with a mortar and pestle, mixed with potassium bromide (KBr) and pressed into a KBr disc using a hydraulic press. The IR spectrum was measured on an FT-IR spectrum at 4 $cm^{-1}$ resolution in the wavenumber range of at least 650 to 4000 $cm^{-1}$ as recommended in the current United States Pharmacopeia (USP). A Digilab Excalibur FTS-4000 FT-IR spectrometer was used. Spectrophotometric grade KBr powder (Thermo Spectra-Tech) along with a Specac Automatic Hydraulic Press (Graseby Specac Limited) was used to prepare the KBr discs.

Example 22

Additional Synthetic Scheme for the Preparation 2-Dimethylaminomethyl-9-hydroxythieno[2,3-c]isoquinolin-5(4H)-one

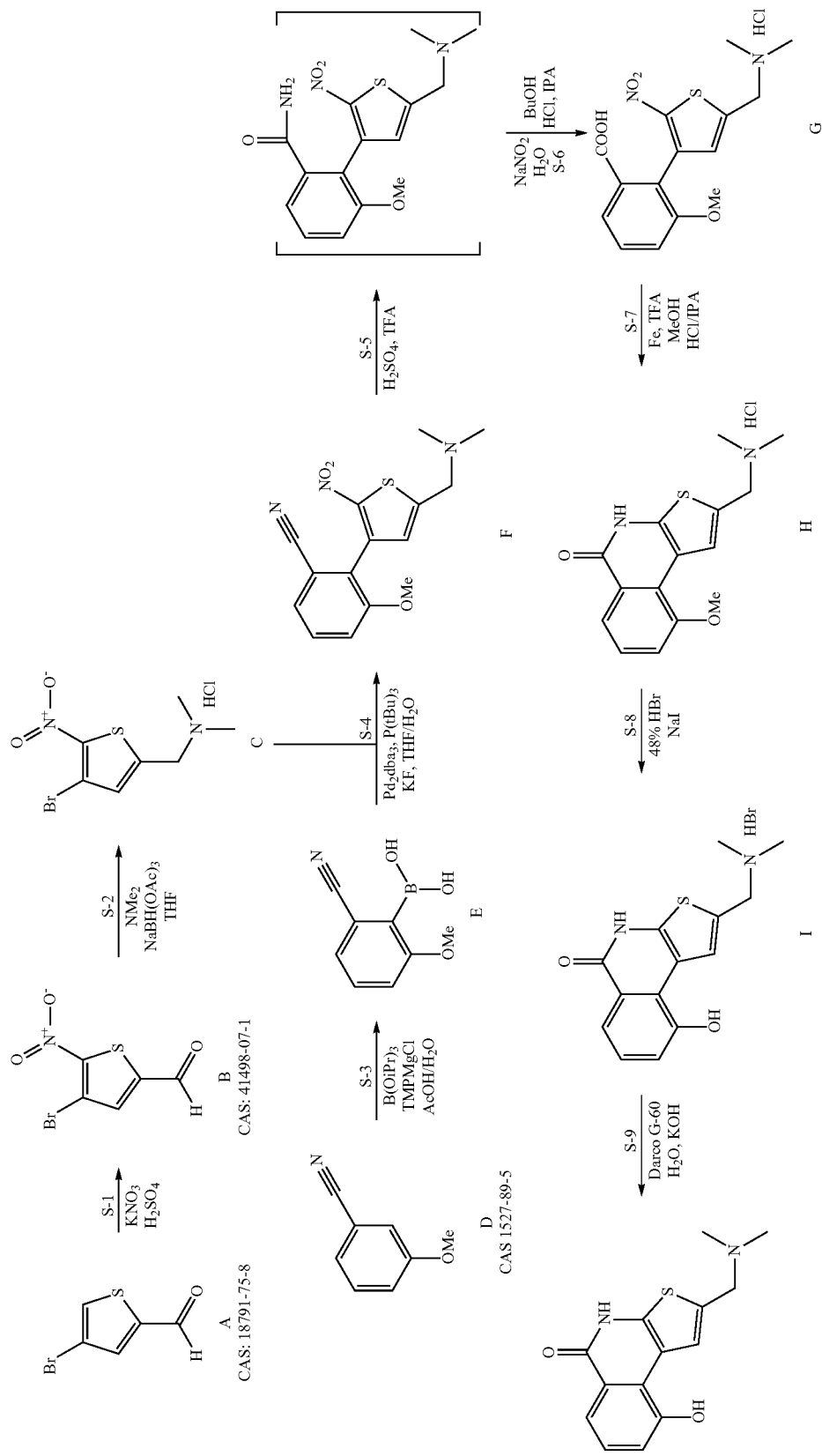

Step S-1: In a 10-L cylindrical reactor, 4-bromo-2-thiophenecarboxaldehyde (Compound A (1.0 kg, 5.23 mol) was dissolved in sulfuric acid (4.0 L) and the solution was cooled to between −10 to 0° C. A solution of potassium nitrate (582 g, 5.76 mol) in sulfuric acid (2.78 L) was then added slowly maintaining the reaction temperature below 0° C. A 10-L cylindrical reactor was charged water (12 L) which was cooled to between 0-5° C. The sulfuric acid solution was then added drop-wise to the reactor containing cold water, maintaining the temperature in the range of between 0-20° C. The resulting slurry was filtered and the product was washed with water (5 L). Compound B (4-bromo-5-nitrothiophene-2-carbaldehyde) was isolated (1.22 kg (98%)) as a pale yellow solid.

Step S-2: Conversion of Compound B to Compound C can be achieved by the addition of dimethylamine as a solution in THF or as neat gas to a solution of Compound B in an appropriate solvent including THF, DCE, toluene or other ethereal solvent at between 0-30° C. An appropriate borohydride or borane reducing agent such as sodium cyanoborohydride, sodium triacetoxyborohydride, borane-pyridine or other borane amine complex can be added. The product can be isolated by extraction into a non-polar solvent such as toluene or MTBE and followed by the addition of anhydrous HCl. For example, in a 5-L cylindrical reactor, Compound B (500 g, 2.12 mol) obtained from step S-1 was taken up in tetrahydrofuran (THF) (1.5 L). The solution was cooled to between 0-10° C. and a solution of dimethyl amine in THF (2.0 M, 1.3 L, 2.75 mol) was added over 1 hour. Sodium triacetoxyborohydride (860 g, 4.24 mol) was added portion-wise maintaining the reaction in the range of between 0-10° C. After 30 minutes, the reaction was quenched with 1 M KOH (1.0 L) and was allowed to warm to room temperature. Toluene (1.0 L) was added and the layers were separated. The organic layer was washed twice with 1 M KOH (1.0 L). The solution was concentrated to a volume of 2 L and the THF was removed with successive charges of toluene. To this solution was added a solution of HCl in isopropanol (5-6 N, 700 mL). The resulting slurry was filtered and washed with toluene. Compound C (1-(4-bromo-5-nitrothiophen-2-yl)-N,N-dimethylmethanamine hydrochloride) was isolated (379 g (60%)) as a yellow solid.

Step S-3: Conversion of Compound D to Compound E can be achieved by metallation of Compound D using a hindered amine base such as lithium tetramethylpiperidide or lithium diisopropylamine at about −78° C. and quenching with an alkyl borate such as trimethyl or triisopropyl borate. Alternatively, the metallation can be achieved at ambient temperature using a solution of tetramethylpiperidine magnesium chloride-lithium chloride complex in THF/toluene. Compound E can be isolated from water as the boronic acid by quenching with an aqueous acid and distilling the organic solvents. For example, a 5-L cylindrical reactor was charged with a solution of tetramethylpiperidine magnesium chloride (TMP-MgCl) (18 wt %, 1.96 L, 1.77 mol) in THF/toluene. The solution was cooled to 15° C. and 3-methoxybenzonitrile (Compound D) (200 g, 1.47 mol) was added over 30 minutes. The solution was stirred at 20° C. for 30 minutes before triisopropylborate (360 g, 1.91 mol) was added. After an additional 30 minutes, the reaction was quenched with acetic acid (354 g, 5.88 mol) and water (1.6 L). The solution was concentrated to remove organic solvent. The resulting slurry was filtered and washed with water. Compound E (2-cyano-6-methoxyphenylboronic acid) was isolated 226 g (86%) as a light tan solid.

Step S-4: The synthesis of Compound F can be achieved through Suzuki coupling of Compounds C and E using a palladium catalyst, a bulky phosphine ligand and inorganic base. Appropriate palladium catalysts include $Pd(PPh_3)_4$, $Pd_2(dba)_3$ or $Pd(OAc)_2$. Effective phosphine ligands include $P(tBu)_3$, $PCy_3$ or bidentate phosphine ligands such as BINAP. Sodium or potassium fluoride are highly effective as inorganic bases. The reaction rate can be accelerated by addition of 5-30% water to the THF solution. Boronate ester derivatives of Compound E such as the pinacol or neopentylglycol esters are also effective as coupling partners. For example, a 5-L cylindrical reactor was charged with Compound C (250 g, 0.83 mol) from step S-2, Compound E from step S-3 (176 g, 0.99 mol) and potassium fluoride (159 g, 2.73 mol). THF (2.0 L) was charged along with water (250 mL) to for a solution. The solution was degassed by sparging nitrogen through the solution for 15 minutes. Tri-t-butylphosphine tetrafluoroborate (4.81 g, 16.5 mmol) and dibenzylideneacetone dipalladium (7.59 g, 8.29 mmol) were charged and the solution stirred for 2 hours until the reaction was complete. Toluene (1.0 L) was added and the solution was washed with 0.25 M $K_3PO_4$ solution (3×500 mL). The solution was concentrated to a volume of 1.0 L and the THF removed with successive charges of toluene. Heptane (1.0 L) was then added slowly, precipitating the product. The slurry was filtered and washed with heptane. Compound F (2-(5-((dimethylamino)methyl)-2-nitrothiophen-3-yl)-3-methoxybenzonitrile) was isolated (221 g (84%)) as a light yellow solid.

Step S-5,6: Hydrolysis of Compound F to Compound G can be achieved by heating an aqueous solution containing acetic acid and other strong acids such as sulfuric, phosphoric or hydrobromic acids to 100-120° C. Milder conditions involve the use of trifluoroacetic acid with another strong non-aqueous acid such as sulfuric, phosphoric or polyphosphoric acid to achieve partial hydrolysis to the amide at between 50-80° C. followed by treatment with aqueous sodium nitrate. For example, Compound F (100 g, 0.32 mol) was taken up in trifluoroacetic acid (500 mL). Sulfuric acid (84 mL) was added and the solution was heated to reflux (75° C.). The reaction was stirred for 8-10 hours until starting the material was consumed. The reaction was cooled to between 0-10° C. and water (50 mL) was added. A solution of sodium nitrite (26.1 g, 0.38 mol) in water (300 mL) was added over 1 hour and the reaction was stirred at 5° C. for an additional 1 hour. 1-Butanol (500 mL) was added and the solution was warmed to room temperature. The aqueous layer was removed and the organic layer was washed with 10% sodium chloride solution (400 mL). The solution was concentrated to a volume of 500 mL. A solution of HCl in isopropanol (5-6 N, 100 mL) was added precipitating the product. The slurry was filtered and washed with 1-butanol. Compound G (2-(5-((dimethylamino)methyl)-2-nitrothiophen-3-yl)-3-methoxybenzoic acid hydrochloride) was isolated (88 g (75%)) as a pale yellow solid.

Step S-7: The reduction of Compound G and cyclization to form Compound H can be achieved through catalytic hydrogenation with a solid supported palladium or platinum catalyst in fluorinated solvent such as trifluoroacetic acid or 2,2,2-trifluoroethanol. The reduction also occurs with a reducing metal such as iron or zinc powder in acidic solutions. Suitable acids include aqueous HCl, HBr and $NH_4Cl$ or non-aqueous carboxylic acids such as acetic acid or trifluoroacetic acid. For example, a 1-L round-bottom flask was charged with iron powder (24 g) and trifluoroacetic acid (110 mL). A solution of Compound G (53.55 g, 144 mmol) in trifluoroacetic acid (160 mL) was then added slowly allowing the temperature to rise to between 50-60° C. The reaction was stirred at 50° C. for 30 minutes and was allowed to cool to room temperature. (Alternatively, the iron powder can be added portion-wise to a solution of Compound G in trifluoroacetic acid at 50° C.) Methanol (100 mL) was added and the excess iron was removed by filtration through celite. The filter was washed with methanol (200 mL). A solution of HCl in isopropanol (50 mL, 5-6 N solution) was added to the filtrate solution and the resulting slurry was filtered and washed with methanol (200 mL). Compound H (2-((dimethylamino)methyl)-9-methoxythieno[2,3-c]isoquinolin-5(4H)-one hydrochloride) was isolated (40.64 g (87%)) as an off-white solid.

Step S-8: Demethylation of Compound H occurs under acidic conditions using an appropriate Lewis acid such as $BBr_3$ or bronstead acid such as HBr. Addition of 1 equivalent of sodium iodine was found to increase the reaction rate. For example, Compound H (40 g, 123 mmol) and sodium iodide (20.3 g, 135 mmol) were taken up in 48% aqueous HBr (450 mL). The solution was heated to 120° C. and stirred at that temperature 6 hours. The product was crystallized by slowly cooling the solution to room temperature over 2 hours. The resulting thick slurry was diluted with methanol (50 mL) and the product filtered and washed with acetone (200 mL). Compound I (2-((dimethylamino)methyl)-9-hydroxythieno[2,3-c]isoquinolin-5(4H)-one hydrobromide) was isolated (35 g (80%)) as a pale green solid.

Step S-9: Compound I (35 g, 98 mmol) was slurried in water (350 mL). The slurry was heated to 80° C. until the solution became homogenous. Darco-G60 (35 g) was added and the solution was stirred for 1 hour. The hot solution was filtered and washed with water (50 mL). The filtrate was cooled to room temperature. To the resulting slurry was added 50% aq. KOH until the pH=10. The slurry was filtered and washed with water (70 mL) and ethyl acetate (50 mL). 2-((dimethylamino)methyl)-9-hydroxythieno[2,3-c]isoquinolin-5(4H)-one was isolated (19.7 g (73%)) as an off-white solid.

Example 23

In Vivo Characterization and Analysis of 2-Dimethylaminomethyl-9-hydroxythieno[2,3-c]isoquinolin-5(4H)-one In vivo efficacy assessments were made using four independent well known models of ischemia.
Materials and Methods
Animals.

Adult male Wistar rats (Charles River, Wilmington, Mass.) 290-310 g were used in all studies. Animal procedures were approved by the Institutional Animal Care and Use Committee and conducted in accordance with the guidelines of the National Institutes of Health.
Transient Middle Cerebral Artery Occlusion (tMCAO).

Rats were anesthetized with 3% isoflurane in a mixture of 70% nitrous oxide and 30% oxygen through a nose cone. Core body temperature was maintained at 37° C. throughout the surgery using a heating lamp. tMCAO was induced for 90 min using the intraluminal suture method (Longa et al., Reversible middle cerebral artery occlusion without craniectomy in rats. Stroke 20:84-91, 1989). Briefly, an 18 mm length of 4-0 monofilament nylon suture coated with poly-L-lysine (Belayev et al., 1996) with a flame-rounded tip was inserted into the external carotid artery and advanced into the internal carotid to occlude the origin of the MCA Ninety minutes later rats were re-anesthetized, the suture withdrawn and the incision closed. Drug (test compound) or vehicle, were administered into the tail vein as a 3 IV bolus doses 3 hours apart in a volume of 2 ml/kg starting at 4 hours post-induction of stroke at various time intervals after the induction of stroke. Animals were tested for motor deficits using a scoring system described by (Bederson et al., 1986). A Bederson score of 5 (maximum) at 90 minutes post-induction of tMCAO was a criterion for inclusion in the trial. Motor deficits and body weight were monitored at 24 and 48 hours post-tMCAO. Neurological deficits were assessed by blinded operators. Rats were sacrificed at 48 hours post-tMCAO. Sham-operated controls were subjected to identical surgical procedures but without advancement of the monofilament into the MCA branching point. The same model was also used, but in addition to occlusion of middle cerebral arteries, both carotid arteries were occluded (CCAO) for the same time 90 minutes. This was Severe Transient MCAO.
Permanent Middle Cerebral Artery Occlusion (pMCAO).

Craniotomy was performed under isoflurane anesthesia. This was followed by electrocauterization of the distal portion of the MCA and a 90 minute ligation of both carotid arteries to limit collateral circulation during the initial stage of stroke, as described by Chen, et al. (Chen et al., 1986). Compound or vehicle, were administered as infusion starting at 4 hours post-induction of stroke and lasting 24 hours. Animals were maintained for long-term functional recovery assessment. Sensorimotor and reflex deficits were evaluated at 3-day intervals for 90 days according to (Bederson et al., 1986; De Ryck et al., 1989). Each trial included: postural test, two visual and two tactile forelimb placement tests and a hind limb placement test. Performance at each test was scored from 0 (no deficit) to 2 (severe deficit) for a maximum combined score of 12. Neurological scoring was performed in a blinded fashion.

A severe permanent model of focal ischemia was used in which the inserted intraluminal suture was not removed and animals were sacrificed at 24 hours post-induction of ischemia for infarct volume measurement. In that model, the compound was administered as 3 IV boluses starting at 30 minutes post in 3 hour intervals.
Infarct volume analysis.

After sacrifice, brains were extracted and 2 mm coronal sections were cut starting at 4 mm from the frontal pole using a rat brain matrix (Stoeling, Wood Dale, Ill.). Sections were stained by immersion in a 2% solution of 2,3,5-triphenyl tetrazolium chloride at 37° C. for 10 minutes and then in 10% neutral formalin for preservation. Digitized images of sections were collected using the MCID image analysis system (Imaging Research, Inc. Ontario, Canada), and the area of infarct determined for each slice. Total infarct volume was calculated by multiplying a sum of areas by the distance between them in mm.
Statistical Analysis.

Values are expressed as means±SEM for the indicated number of animals or number of in vitro experiments. The statistical significance of differences between means was calculated by one-way ANOVA with post-hoc Fisher test or Dunnett's comparison to control or with Student's t-test analysis, as appropriate. Linear mix model was used to assess differences between treatment groups during 3-week neurological function recovery testing post-pMCAO. Statistical significance was assumed at $p<0.05$.

The first study was conducted using a transient middle cerebral artery occlusion (tMCAO) model. Rats were subjected to 90 minutes tMCAO and compound (2-dimethylaminomethyl-9-hydroxythieno[2,3-c]isoquinolin-5(4H)-one) was administered using 3 bolus injections at 4, 7 and 10 hours post-ischemia and an intraperitoneal (IP) route of administration. The three doses evaluated were 0.1, 1 and 10 mg/kg. Dosing was initiated at 4 hours post-MCAO because it is a clinically relevant therapeutic time window to treatment. Infarct volumes and neurological testing were carried out at 48 hours post-ischemia. This model produces an extensive unilateral lesion that involves the motor cortex and striatum. It is used to assess acute neuroprotection and neurological function in a reperfusion model of stroke.-

Rats that received 3×0.1, 1 or 10 mg/kg IP 2-dimethylaminomethyl-9-hydroxythieno[2,3-c]isoquinolin-5(4H)-one had significantly reduced infarct volumes by 20, 55 and 66%, respectively, at 48 hours following tMCAO compared to vehicle-treated rats. In addition, rats treated with 1 mg/kg 2-dimethylaminomethyl-9-hydroxythieno[2,3-c]isoquinolin-5(4H)-one also displayed significantly reduced neurological deficits at 48 hr post-MCAO A severe, permanent MCAO study was also conducted using a 1 mg/kg dose delivered IP in 3 boluses, the first at 30 minutes post-ischemia, followed at 3.5 and 8 hours with evaluation of infarct at 24 hours post-ischemia. The injury produces an extensive infarct that encompasses much of the ischemic hemisphere and induces severe inflammation. Rats subjected to this insult have high mortality beyond 24 hours which precluded neurological testing. This model is accepted by those skilled in the art as supporting the use of 2-dimethylaminomethyl-9-hydroxythieno[2,3-c]isoquinolin-5(4H)-one in the treatment of stroke patients without reperfusion.

Rats treated with 3×1 mg/kg 2-dimethylaminomethyl-9-hydroxythieno[2,3-c]isoquinolin-5(4H)-one had significantly smaller infarct volumes (42% smaller) than vehicle-treated rats.

In a third assay, a severe tMCAO model was used (where both MCAO and carotid arteries were temporarily occluded) to obtain an injury. 2-Dimethylaminomethyl-9-hydroxythieno[2,3-c]isoquinolin-5(4H)-one was administered by multiple IV boluses. Doses of 1 or 10 mg/kg of 2-dimethylaminomethyl-9-hydroxythieno[2,3-c]isoquinolin-5(4H)-one were given at 4, 7 and 10 hours and animals were evaluated for infarct size, weight loss and neurological score at 48 hours post-MCAO.

Treatment with 3 times 1 or 10 mg/kg of 2-dimethylaminomethyl-9-hydroxythieno[2,3-c]isoquinolin-5(4H)-one resulted in a significantly reduced infarct volume (22% smaller volume for 1 mg/kg and 19% smaller for 10 mg/kg), reduction of neurological deficits and reduction of ischemia-induced weight loss at 48 hours following tMCAO.

A further efficacy study was conducted and employed a less severe permanent MCAO (pMCAO) model. This model, which utilized an occlusion of the distal portion of the middle cerebral artery, produced a much smaller injury contained within the sensorimotor cortex of the animal. The injury sustained in this model was less extensive but still involves the motor cortex and the rats can be assessed over the long-term (3 weeks to 3 months post-ischemia) for neurological function. In a first study with this model, rats were administered an IV bolus dose of 1, 3 or 10 mg/kg initiated at 4 hours post-ischemia and followed by 2 subsequent and equivalent doses at 7 and 10 hours. In a second study, rats were given a single IV bolus followed by a 24 hr IV infusion. Neurological function was tested every 2-3 days for 3 weeks post-MCAO.

Using the multiple IV bolus dosing paradigm in this model, no significant improvement in neurological function was found at 21 days post-ischemia although the 10 mg/kg dose approached efficacy. In the second pMCAO study, rats that received 2-dimethylaminomethyl-9-hydroxythieno[2,3-c]isoquinolin-5(4H)-one at a dose of 3.5 mg/kg IV bolus plus 2.5 mg/hr IV infusion for 24 hours had significantly reduced neurological deficits when measured at 39 days post-ischemia and this recovery was maintained for at least 3 months following ischemia.

Finally, rats were tested in an IV bolus plus 24 hour infusion paradigm with 2 lower doses of 2-dimethylaminomethyl-9-hydroxythieno[2,3-c]isoquinolin-5(4H)-one in the tMCAO model. The tMCAO model produced robust efficacy following multiple IV bolus injections. Rats were given 3.9 mg/kg IV bolus followed by infusion of 0.3 mg/hr for 24 hours or 11.7 mg/kg bolus followed by infusion of 0.9 mg/hr for 24 hours. Drug or vehicle (saline given at the same volume and rate of infusion) administration was initiated 4 hours post-tMCAO. Rats that received the higher of the two doses of 2-dimethylaminomethyl-9-hydroxythieno[2,3-c]isoquinolin-5(4H)-one (11.7 mg/kg bolus followed by infusion of 0.9 mg/hr for 24 hours) displayed a significant reduction in neurological deficits at 48 hours, a significant reduction in ischemic-induced weight loss and a small but insignificant reduction in infarct volume (10%). No effect was seen in the lower of the two doses.

Table 6 provides a summary of in vivo efficacy observed in these studies.

TABLE 6

Summary of In Vivo Efficacy

| Model | Efficacious Dose |
| --- | --- |
| tMCAO MED (4 hr) | 3 × 1 mg/kg, ip |
| pMCAO MED (30 min) | 3 × 1 mg/kg, ip |
| tMCAO MED (4 hr) | 3 × 1 mg/kg, iv |
| pMCAO MED (4 hr) | 3.5 mg/kg, iv bolus/2.5 mg/hr, iv infusion |

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of treating tissue damage due to ischemia and reperfusion, of inhibiting neuronal cell death due to ischemia and reperfusion, or both, in a subject in need thereof comprising administering to the subject a therapeutically effective amount of a compound of Formula I:

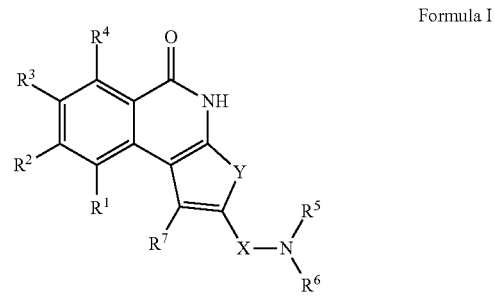

Formula I wherein:
X is $C_1$-$C_9$ alkylene, $C_2$-$C_9$ alkenylene, or $C_2$-$C_9$ alkynylene;
Y is S or O;
$R^1$ is halogen, hydroxy, $NH_2$, $C_1$-$C_6$ alkoxy, CN, or $C_1$-$C_6$ perfluoroalkyl;
$R^2$, $R^3$, and $R^4$ are each, independently, selected from hydrogen, $C_1$-$C_6$ alkyl, halogen, hydroxy, $NH_2$, CN, $C_1$-$C_6$ perfluoroalkyl, $CO_2H$, $OR^8$, $COOR^8$, and $NHR^8$;
$R^5$ and $R^6$ are each, independently, selected from hydrogen, $C_1$-$C_6$ alkyl, $C_2$-$C_4$ alkenyl, $C_3$-$C_7$ cycloalkyl, phenyl, and benzyl, wherein the alkyl, alkenyl and rings of the cycloalkyl, phenyl and benzyl groups are optionally substituted with one or more groups independently selected from hydroxy, $C_1$-$C_4$ alkoxy, —$CO_2H$, $C_1$-$C_6$ alkoxycarbonyl, $NH_2$, $C_1$-$C_6$ mono- or dialkylamino, and halogen; or $R^5$ and $R^6$ together with the nitrogen to which they are attached form a saturated, partially unsaturated, or unsaturated 3 to 12 membered monocyclic or bicyclic heterocyclic ring optionally comprising from one to three additional ring heteroatoms independently selected from N, O, and S, the remaining ring atoms are carbon atoms;

$R^7$ is hydrogen, halogen, hydroxy, $NH_2$, $C_1$-$C_3$ alkyl, $C_1$-$C_3$ alkoxy or $NO_2$;

$R^8$ is $C_1$-$C_6$ alkyl, $C_2$-$C_6$ alkenyl, or $C_3$-$C_7$ cycloalkyl wherein the alkyl, alkenyl, and rings of the cycloalkyl are optionally substituted with one or more groups independently selected from hydroxy, $C_1$-$C_4$ alkoxy, —$CO_2H$, $C_1$-$C_6$ alkoxycarbonyl, $NH_2$, $C_1$-$C_6$ mono- or dialkylamino, and halogen;

or a pharmaceutically acceptable salt or zwitterionic form thereof.

2. The method according to claim 1, wherein

X is $C_1$-$C_9$ alkylene, $C_2$-$C_9$ alkenylene, or $C_2$-$C_9$ alkynylene;

Y is S or O;

$R^1$ is halogen, hydroxy, $NH_2$, $C_1$-$C_6$ alkoxy, CN, or $C_1$-$C_6$ perfluoroalkyl;

$R^2$, $R^3$, and $R^4$ are each, independently, selected from hydrogen, halogen, hydroxy, $NH_2$, $C_1$-$C_6$ alkoxy, CN, and $C_1$-$C_6$ perfluoroalkyl;

$R^5$ and $R^6$ are each, independently, selected from hydrogen, $C_1$-$C_6$ alkyl, $C_2$-$C_4$ alkenyl, $C_3$-$C_7$ cycloalkyl, phenyl, and benzyl; or $R^5$ and $R^6$ together with the nitrogen to which they are attached form a saturated, partially unsaturated, or unsaturated 3 to 12 membered monocyclic or bicyclic heterocyclic ring optionally comprising from one to three additional ring heteroatoms selected from N, O, and S, the remaining ring atoms are carbon atoms; and $R^7$ is hydrogen, halogen, hydroxy, $NH_2$, $C_1$-$C_3$ alkyl, $C_1$-$C_3$ alkoxy or $NO_2$; or a pharmaceutically acceptable salt or zwitterionic form thereof.

3. The method according to claim 1, wherein the compound is:

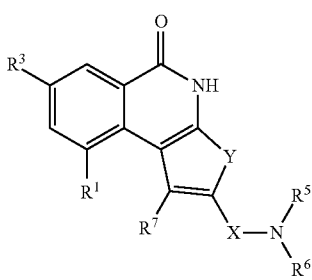

Formula II or a pharmaceutically acceptable salt or zwitterionic form thereof.

4. The method according to claim 1, wherein the compound is:

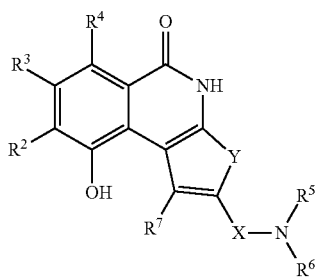

Formula III or a pharmaceutically acceptable salt or zwitterionic form thereof.

5. The method according to claim 1, wherein the compound is:

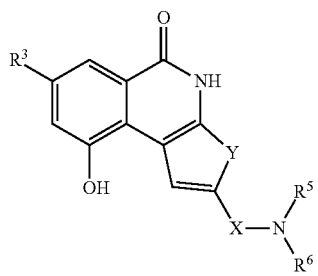

Formula IV or a pharmaceutically acceptable salt or zwitterionic form thereof.

6. The method according to claim 5, wherein $R^3$ is halogen or hydrogen.

7. The method according to claim 6, wherein $R^3$ is hydrogen.

8. The method according to claim 1, wherein Y is S.

9. The method according to claim 1, wherein Y is O.

10. The method according to claim 1, wherein $R^5$ and $R^6$ are each, independently, $C_1$-$C_6$ alkyl.

11. The method according to claim 1, wherein $R^5$ and $R^6$ together with the nitrogen to which they are attached form a saturated monocyclic heterocyclic ring optionally comprising from one to three additional ring heteroatoms selected from N, O, and S, the remaining ring atoms are carbon atoms.

12. The method according to claim 11, wherein $R^5$ and $R^6$ are taken together to form piperidine, morpholine, pyrrolidine, homopiperidine, aziridine, or azetidine.

13. The method according to claim 1, wherein X is $C_1$-$C_3$ alkylene.

14. The method according to claim 1, wherein X is $C_1$-$C_3$ alkylene and $R^5$ and $R^6$ are each, independently, $C_1$-$C_6$ alkyl.

15. The method according to claim 1, wherein X is methyl.

16. The method according to claim 1, wherein X is methyl and $R^5$ and $R^6$ are each, independently, methyl.

17. The method according to claim 1, wherein:

Y is S;

X is $C_1$-$C_3$ alkylene; and $R^5$ and $R^6$ are each, independently, $C_1$-$C_6$ alkyl.

18. The method according to claim 17, wherein X is methyl.

19. The method according to claim 1, wherein:
Y is O;
X is $C_1$-$C_3$ alkylene; and
$R^5$ and $R^6$ are each, independently, $C_1$-$C_6$ alkyl.

20. The method according to claim 19, wherein X is methyl.

21. The method according to claim 1, wherein the compound is:
2-dimethylaminomethyl-9-methoxythieno[2,3-c]isoquinolin-5(4H)-one;
8-chloro-2-[(dimethylamino)methyl]thieno[2,3-c]isoquinolin-5(4H)-one; or
2-[(dimethylamino)methyl]-8-methoxythieno[2,3-c]isoquinolin-(4H)-one; or
a pharmaceutically salt or zwitterionic form thereof.

22. The method according to claim 1, wherein the compound is:
2-dimethylaminomethyl-9-hydroxythieno[2,3-c]isoquinolin-5(4H)-one or a pharmaceutically acceptable salt or zwitterionic form thereof.

23. The method according to claim 1, wherein the compound is:
amorphous 2-dimethylaminomethyl-9-hydroxythieno[2,3-c]isoquinolin-5(4H)-one or a pharmaceutically acceptable salt or zwitterionic form thereof.

24. The method according to claim 1, wherein the compound is:
2-dimethylaminomethyl-9-hydroxythieno[2,3-c]isoquinolin-5(4H)-one hydrate.

25. The method according to claim 1, wherein the compound is: 2-dimethylaminomethyl-9-hydroxythieno[2,3-c]isoquinolin-5(4H)-one monohydrate.

26. The method according to claim 1, wherein the compound is:
2-dimethylaminomethyl-9-hydroxythieno[2,3-c]isoquinolin-5(4H)-one monohydrate having an endotherm at about 139° C.

27. The method according to claim 1, wherein the compound is:
2-dimethylaminomethyl-9-hydroxythieno[2,3-c]isoquinolin-5(4H)-one anhydrate.

28. The method according to claim 1, wherein the compound is:
2-dimethylaminomethyl-9-hydroxythieno[2,3-c]isoquinolin-5 (4H)-one anhydrate having endotherms at about 210° C. and 270° C.

29. The method according to claim 1, wherein the compound comprises a crystalline anhydrous form of 2-dimethylaminomethyl-9-hydroxythieno[2,3-c]isoquinolin-5(4H)-one thereof having an X-ray powder diffraction containing at least 3 characteristic 2θ values measured using CuKα radiation selected from 10.4, 10.6, 14.5, 21.3, 26.8 and 32.1.

30. The method according to claim 1, wherein the compound comprises a crystalline monohydrate form of 2-dimethylaminomethyl-9-hydroxythieno[2,3-c]isoquinolin-5 (4H)-one thereof having an X-ray powder diffraction containing at least 3 characteristic 2θ values measured using CuKα radiation selected from 8.3, 8.6, 11.7, 18.4, 18.9, 19.4, 25.7 and 28.7.

31. The method according to claim 1, wherein the compound is:
2-[(dimethylamino)methyl]-7-fluoro-9-hydroxythieno[2,3-c]isoquinolin-5(4H)-one; or
a pharmaceutically acceptable salt or zwitterionic form thereof.

32. The method according to claim 1, wherein the compound is:
2-[(dimethylamino)methyl]-7-fluorothieno[2,3-c]isoquinolin-5(4H)-one;
2-[(dimethylamino)methyl]-9-fluorothieno[2,3-c]isoquinolin-5(4H)-one;
or 2-[(dimethylamino)methyl]furo[2,3-c]isoquinolin-5 (4H)-one hydrochloride; or
a pharmaceutically acceptable salt or zwitterionic form thereof.

33. The method according to claim 1, wherein the compound is:
9-hydroxy-2-(morpholin-4-ylmethyl)thieno[2,3-c]isoquinolin-5(4H)-one;
9-hydroxy-2-(piperidin-1-ylmethyl)thieno[2,3-c]isoquinolin-5 (4H)-one;
9-hydroxy-2-(1,3-thiazolidin-3-ylmethyl)thieno[2,3-c]isoquinolin-5(4H)-one;
9-hydroxy-2-{[(1-methylethyl)amino]methyl}thieno[2,3-c]isoquinolin-5(4H)-one;
9-hydroxy-2-(pyrrolidin-1-ylmethyl)thieno[2,3-c]isoquinolin-5(4H)-one;
2-[(4-bromopiperidin-1-yl)methyl]-9-hydroxythieno[2,3-c]isoquinolin-5(4H)-one;
2-[(dibenzylamino)methyl]-9-hydroxythieno[2,3-c]isoquinolin-5 (4H)-one;
2-{[benzyl(methyl)amino]methyl}-9-hydroxythieno[2,3-c]isoquinolin-5 (4H)-one;
or a pharmaceutically acceptable salt or zwitterionic form thereof.

34. The method according to claim 1, wherein the compound comprises a zwitterion of 2-dimethylaminomethyl-9-hydroxythieno[2,3-c]isoquinolin-5(4H)-one.

35. The method according to claim 1, wherein the compound comprises a crystalline anhydrous form of 2-dimethylaminomethyl-9-hydroxythieno[2,3-c]isoquinolin-5(4H)-one with an average particle size of about 5 to 10 μm and more particularly about 7 μm.

36. The method according to claim 1, wherein the compound comprises a crystalline anhydrous form of 2-dimethylaminomethyl-9-hydroxythieno[2,3-c]isoquinolin-5(4H)-one characterized by orthorhombic agglomerations with an average length of about 5 to 10 μm and more particularly about 6 p.m.

37. The method according to claim 1, wherein the compound is:
2-[(dimethylamino)methyl]thieno[2,3-c]isoquinolin-5 (4H)-one or a pharmaceutically acceptable salt or zwitterionic form thereof.

* * * * *